US008143389B2

(12) United States Patent
Shaw et al.

(10) Patent No.: US 8,143,389 B2
(45) Date of Patent: Mar. 27, 2012

(54) INHIBITON OF METALLO-β-LACTAMASE BY DOUBLE-STRANDED DNA

(75) Inventors: Robert W. Shaw, Lubbock, TX (US); Mitchel Cottenoir, Roswell, NM (US)

(73) Assignee: Texas Tech University, Lubbock, TX (US)

( * ) Notice: Subject to any disclaimer, the term of this patent is extended or adjusted under 35 U.S.C. 154(b) by 626 days.

(21) Appl. No.: 11/990,811

(22) PCT Filed: Aug. 24, 2006

(86) PCT No.: PCT/US2006/033029
§ 371 (c)(1),
(2), (4) Date: Apr. 7, 2008

(87) PCT Pub. No.: WO2007/025016
PCT Pub. Date: Mar. 1, 2007

(65) Prior Publication Data
US 2010/0261777 A1 Oct. 14, 2010

Related U.S. Application Data

(60) Provisional application No. 60/711,129, filed on Aug. 25, 2005.

(51) Int. Cl.
*C07H 21/04* (2006.01)
(52) U.S. Cl. .................... 536/24.5; 536/23.1
(58) Field of Classification Search .................. None
See application file for complete search history.

(56) References Cited

U.S. PATENT DOCUMENTS
7,456,274 B2 11/2008 Shaw

OTHER PUBLICATIONS

Allawi, H. T. and SantaLucia, J. Jr. (1997), "Thermodynamics and NMR of Internal G-T Mismatches in DNA", Biochemistry 36, 10581-10594.
Ambler, R. P., Daniel, M., Fleming, J., Hermoso, J. -M., Pang, C. and Waley, S. G. (1985), "The Amino Acid Sequence of the Zinc-Requiring β-Lactamase II from the bacterium *Bacillus cereus*", FEBS Lett. 189, 207-211.
Bartel, D. P. and Szostak, 1. W., (1993), "Isolation New Ribozymes from a Large Pool of Random Sequences", Science 261, 1411-1418.
Bicknell, R., Schaeffer, A., Waley, S. G. and Auld, D. S. (1986), "Changes in the Coordination Geometry of the Active-Site Metal During Catalysis of Benzylpenicillin Hydrolysis by *Bacillus cereus* β-Lactamase II", Biochemistry 25, 7208-7215.
Bock, L. C., Griffin, L. c., Latham, J. A., Vermass, E. H. and Toole, J. J. (1992), "Selection of Single-Stranded DNA Molecules that bind and Inhibit Human Thrombin", Nature 355, 564-566.
Chen, H. and Gold, L., (1994), "Selection of High-Affinity RNA Ligands to Reverse Transcriptase", Biochemistry 33, 8746-8756.
Concha, N. 0., Janson, C. A., Rowling, P., Pearson, S., Cheever, C. A., Clarke, B. P., Lewis, C., Galleni, M., Frere, J. M., Payne, D. J., Bateson, J. H. and Abdel-Meguid, S. S. (2000), "Crystal of the IMP-I Metallo-β-Lactamase from *Pseudomonas aeruginosa* and its Complex with a Mercaptocarboxvlate Inhibitor", Biochemistry 15, 4288-4298.
Crompton, B., Jago, M., Crawford, K., Newton, G. G. F. and Abraham, E. P. (1962), "Behaviour of Some Derivatives of 7-Aminocephalosporanic Acid as Substrates, Inhibitors and Inducers of Penicillanases", Biochem. J. 83, 52-63.
Davies, R. B. and Abraham, E. P. (1974), "Metal Cofactor Requirements of β-Lactamase II", Biochem. J. 143, 129-135.
Davies, R. B. Abraham, E. P. and Melling, J. (1974), "Separation, Purification and Properties of β-Lactamase I and β-Lactamase II from *Bacillus cereus* 569/H/9", Biochem. J. 143, 115-127.
Davies, R. B. Abraham, E. P. Melling, J. and Pollock, M. R. (1975),"Comparison of β-lactamase II from *Bacillus cereus* 569/H/9 with a β-Lactamase from *Bacillus cereus* 5/B/6", Biochem. J. 145,409-411.
Farmulok, M. and Szostak, J. W. (1992), "In Vitro Selection of Specific Ligand Binding Nucleic Acids", Angew. Chem. Int. Ed. Engl. 31, 979-988.
Felici, A. and Amicosante, G. (1995), "Kinetic Analysis of Extension of Substrate Specificity with *Xanthomonas maltophilia, Aeromonas hydrophylia* and *Bacillus cereus* Metallo-β-Lactamases", Antimicrob. Agents Chemother. 39, 192-199.
Felici, A, Amicosante, G., Oratore, A, Strom, R., Ledent, R, Joris, B., Fanuel, L. and Frere, J. -M. (1993), "An Overview of the Kinetic Parameters of Class B β-Lactamases", Biochem. J. 291, 151-155.
Felici, A, Perilli, M., Franceschini, N., Rossolini, G. M., Galleni, M., Frere, J. -M., Oratore, A and Amicosante, G. (1997), "Sensitivity of *Aeromonas hydrophilia* Carbapenemase to Δ^3-Cephems", Antimicrob. Agents Chemother. 41, 866-868.
Hicke, B. J. and Stephens, A. W. (2000), "Escort Aptamers", J. Clin. Invest. 106, 923-928.
Hilliard, N. P., (1995), "Structure-Function Relationships in the Metallo-13-Lactamase of *Bacillus cereus* 5/B/6", Ph.D. thesis, Texas Tech University.
Hussain, M., Pastor, F. I. J. and Lampen, J. O. (1987), "Cloning and Sequencing of the blaZ Gene Encoding β-Lactamase III, a Lipoprotein of *Bacillus cereus* 569/H", J. Bacteriol. 169, 579-586.
Jaeger, J. A., Turner, D. H. and Zuker, M. (1989), "Improved Predictions of Secondary Structures for RNA", Proc. Natl. Acad. Sci. USA 86, 7706-7710.
Jaeger, J. A, Turner, D. H. and Zuker, M. (1990), "Predicting Optimal and Suboptimal Secondary Structure for RNA", in Methods in Enzymology 183, 281-306.
Jellinek, D., Green, L. S., Bell, C. and Janjic, N. (1994), "Inhibition of Receptor Binding by High-Affinity RNA Ligands to Vascular Endothelial Growth Factor", Biochemistry 33, 10450-10456.
Kogut, M., Pollock, M. R. and Tridgell, E. J. (1956), "Purification of Penicillin-Induced Penicillinase of *Bacillus cereus* NRRL 569", Biochem. J. 62, 391-401.
Kuwabara, S., Adams, E. P. and Abraham, E. P. (1970),"Composition of β-lactamase I and β-Lactamase II from *Bacillus cereus* 569/H", Biochem. J. 118, 475-480.
Kuwabara, S. and Lloyd, P. H. (1971), "Protein and Carbohydrate Moieties of a Preparation of β-Lactamase II", Biochem. J. 124, 215-220.

(Continued)

Primary Examiner — Amy Bowman
(74) Attorney, Agent, or Firm — Roman Aguilera, III

(57) ABSTRACT

Compositions and methods for identifying double stranded DNA molecules that bind with high affinity to metallo-β-lactamase. Methods for inhibiting the activities of the metallo-β-lactamase in bacteria by double stranded DNA molecules.

3 Claims, 19 Drawing Sheets

OTHER PUBLICATIONS

Figure 1:
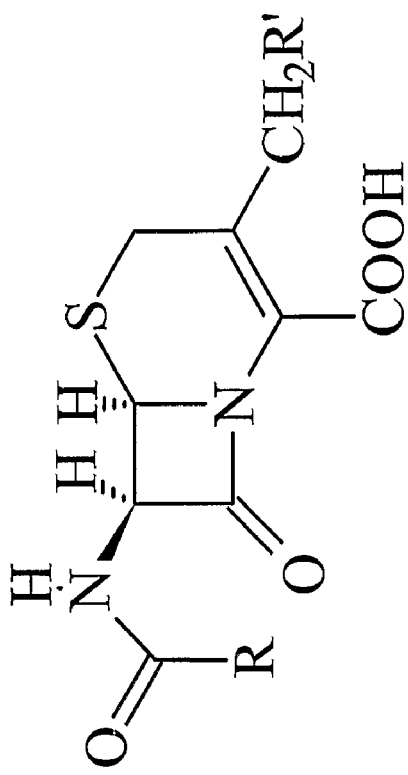
Figure 1:
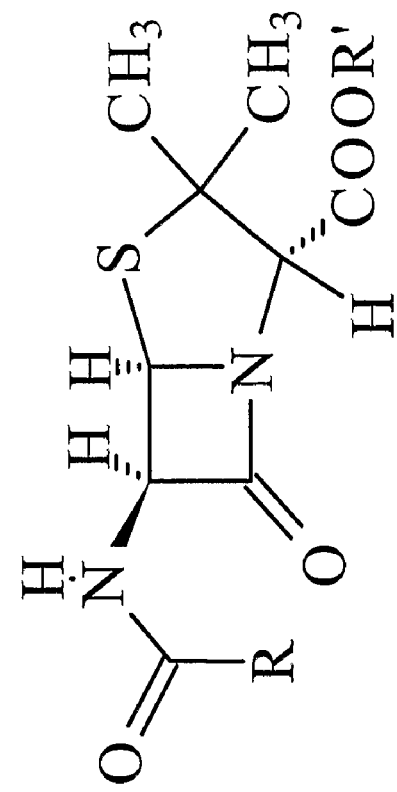

Ledent, R, Raquet, X., Joris, B., Van Beeumen, J. and Frere, 1. -M. (1993), "A Comparative Study of Class D Beta-Lactamases", Biochem. J. 292, 555-562.

Lim, H. M., Pene, J. J. and Shaw, R. W. (1988), "Cloning, Nucleotide Sequence and Expression of the *Bacillus cereus* 5/B/6 β-Lactamase II Structural Gene" 1. Bacteriol. 170, 2873-2878.

Macaya, R. F., Waldron, J. A, Beutel, B. A., Gao, H., Joeston, M. E., Yang, M., Patel, R., Bertelsen, A. H. And Cook, A G. (1995), "Structural and Functional Characterization of Potent Antithrombotic Oligonucleotides Possessing Both Quadruplex and Duplex Motifs", Biochemistry 34, 4478-4492.

Matagne, A., Ledent, P., Monnaie, D., Felici, A., Jamin, M., Raquet, X., Galleni, M., Klein, D., Francois, Land Frere, J. M. (1995), "Kinetic Study of Interaction Between BRL 42715, β-Lactamases and D-Alanyl-D-Alanyl Peptidases", Antimicrob. Agents Chemother. 39, 227-231.

Neu, H. C. (1992), "The Crisis in Antibiotic Resistance", Science 257, 1064-1073.

Payne, D. J. (1993),"Metallo-β-lactamases-A New Therapeutic Challenge", J. Med. Microbiol. 39, 993-999.

Rasmussen, B. A., Yang, Y., Jacobs, N. and Bush, K. (1994), "Contribution of Enzymatic Properties, Cell Permeability and Enzyme Expression to Microbial Activities of Beta-lactams in Three Bacteroides fragilis Isolates that Harbor a Metallo-β-Lactamase gene", Antimicrob. Agents Chemother. 38, 2116-2120.

Robertson, D. L. and Joyce, G. F. (1990), "Selection in vitro of an RNA Enzyme that Specifically Cleaves Single-Stranded DNA", Nature 344, 467-468.

Ruckman, J., Green, L. S., Beeson, J., Waugh, S., Gillette, W. L., Henninger, D. D., Claesson-Welsh, L. and Janjic, N. (1998), "2'-Fluoropyrimidine RNA-Based Aptamers to the 165-Amino Acid Form of Vascular Endothelial Growth Factor (VEGF165)", Journal of Biological Chemistry 273, 20556-20567.

Sabath, L. D. and Abraham, E. P. (1966), "Zinc as a Cofactor for Cephalosporinase from *Bacillus cereus* 569", Biochem. J. 98, 11c-13c.

Sutton, B. J., Artymiuk, P. J., Cordero-Borboa, A. E., Little, C., Philips, D. C. and Waley, S. G. (1987), "X-Ray Crystallographic Study of β-Lactamase II from *Bacillus cereus* at 0.35 nm Resolution", Biochem. J. 248, 181-188.

Tasset, D. M., Kubik, M. F. and Steiner, W. (1997), "Oligonucleotide Inhibitors of Human Thrombin that Bind Distinct Epitopes", J. Mol. Biol. 272, 688-698.

Thatcher, D. R. (1975), "Partial Amino Acid Sequence of the Extracellular β-Lactamase I of *Bacillus cereus* 569/H", Biochem. J. 147, 313-326.

Tsiang, M., Gibbs, C. S., Griffin, L. C., Dunn, K. E. and Leung, L. K. (1995), "Selection of a Suppressor mutation That Restores Affinity of an Oligonucleotide Inhibitor for Thrombin Using in Vitro Genetics", J. Biol. Chem. 270, 19370-19376.

Tuerk, C. and Gold, L. (1990), "Systematic Evolution of Ligands by Exponential Enrichment", Science 249, 505-510.

Turner, D. H., Sugimoto, N. and Freier, S. M. (1988), "RNA Structure Prediction", Annu. Rev. Biophys. Biophys. Chem. 17, 167-192.

Zuber, M., Patterson, T. A. and Court, D. L. (1987),"Analysis of nutR", Proc. Natl. Acad. Sci. USA 84, 4514-4518.

Zuker, M. (1989), "On Finding All Suboptimal Foldings of an RNA Molecule", Science 244, 48-52.

Pitout J. D., Sanders C. C., Sanders W. E. Jr. (1997), "Antimicrobial Resistance with Focus on Beta-lactam Resistance in Gram-Negative Bacilli", Am. J. Med. 103(1): 51-9.

ATGATCCGGTGCTGTATGTTCCTACATGA
||||||||||||||||||||||||||||
TACTCGGCCACGACATACAAGGATGTACT dsDNA 29mer (SEQID No.: 4)

ATGATCCGGTGCTGT
|||||||||||||||
TACTCGGCCACGACA dsDNA 15-mer (SEQID No.: 5)

ATGTTCCTACATGA
||||||||||||||
TACAAGGATGTACT dsDNA 14-mer (SEQID No.: 6)

Figure 19

INHIBITON OF METALLO-β-LACTAMASE BY DOUBLE-STRANDED DNA

This application claims priority to U.S. Provisional Patent Application Ser. No. 60/711,129 filed on Aug. 25, 2005, entitled "Inhibition of Metallo-β-Lactamase by Double-Stranded DNA", the entire content of which is hereby incorporated by reference.

BACKGROUND

This invention pertains to antibacterial compositions and a method of inhibiting bacterial β-lactamases. The prevention and/or treatment of infections in a subject may be accomplished by administering a β-lactamases inhibitor composition that consists of double stranded deoxyribose nucleic acid (DNA) fragments. More specifically, a method of inhibiting a β-lactamases in bacterium includes: contacting the bacterium with an isolated double stranded DNA. In a preferred embodiment, the double stranded DNA is at least 90% identical to SEQ ID No.: 4.

Selecting a site of action is one of the most important decisions made when developing antibacterial compounds. β-lactam antibiotics targets cell wall development, which is one of the most accessible processes of the cell. In 1929, Sir Alexander Fleming indirectly came across these compounds that were produced as a defense mechanism by the fungus *Penicilium notatum*. Since that time β-lactam antibiotics have become some of the most prescribed chemotherapeutic compounds (Maugh, 1981).

β-Lactam antibiotics include penicillins, cephalosporins, monobactams and carbapenems. These compounds are analogs of peptidoglycans, which are essential to the production of the cell wall. The DD-peptidases (D-alanyl-D-alanine carboxypeptidases/transpeptidases) are the target enzymes of the β-lactam antibiotics. These enzymes catalyze the cross-linkage of peptidoglycans during bacterial cell wall biosynthesis. β-lactam antibiotics form a stable covalent acylenzyme complex that has a much longer half-life than that which is formed with the peptidoglycans. This disrupts the synthesis of the cell wall, which eventually leads to cell death (Kelly et al., 1988; Ghuysen, J. M., 1988). Inhibition of cell wall synthesis proves to be a very effective method in disrupting bacterial cell growth. The lack of a cell wall in mammalian cells is paramount because even at high concentrations of the β-lactam antibiotics, mammalian cells are not affected (Maugh, 1981).

Figure 2:
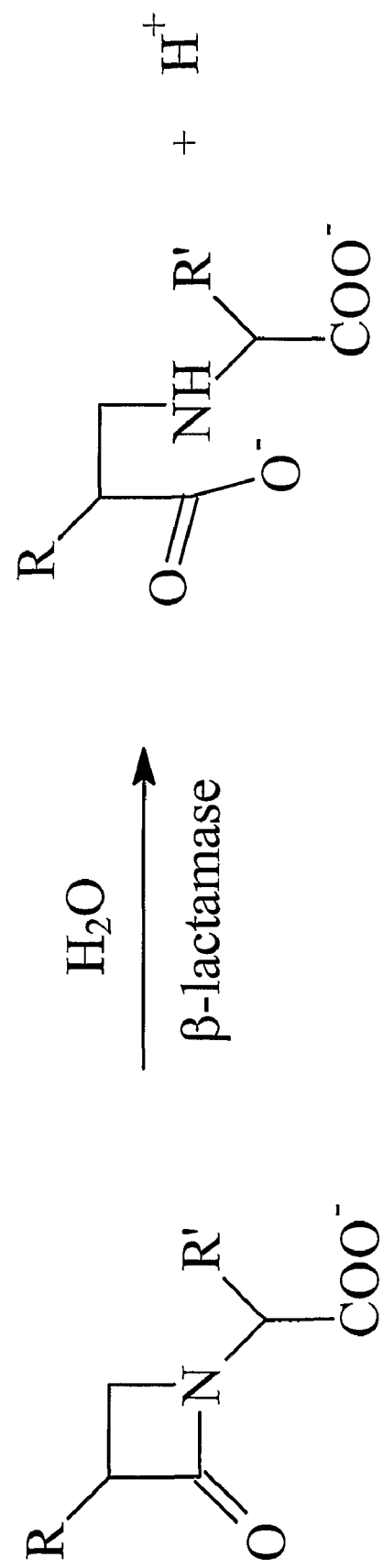

The general structures of penicillin and cephalosporins are shown in FIG. 1. When compared to the structure of peptidoglycans, the ring structure of the β-lactam places strain on the adjacent atoms to have a similar configuration.

β-Lactamases (β-lactamhydrolyases, EC 3.5.2.6) are enzymes that very efficiently catalyze the hydrolysis of the β-lactam ring antibiotics, causing them to lose their bactericidal activity (Fisher et al, 1981, Maugh, 1981) (FIG. 2).

Bacteria that obtain a gene for producing β-lactamases become resistant to β-lactam antibiotics. Many different bacteria have one of these genes including *Bacillus cereus*, *Bacillus anthracis*, *Bacillus fragillis*, *Escherichia coli*, *Bacteriodes*, *Staphlococcus epidermidis*, *Streptococcus*, *Psuedomonas aerugenosa*, *Providencia*, *Haemophilus*, *Xanthomonas maltophilia*, *Acinetobactor*, *Citrobactor*, *Enterobactor*, and *Branhamella* (Danziger and Pendland, 1995). β-Lactamases can be transferred between bacteria when the gene is present on a plasmid. These enzymes are classified based on their primary structure and catalytic properties. Currently there is a four-class system for β-lactamases consisting of A, B, C, and D (Ambler, 1980; Ambler et al., 1991; Joris et al., 1991; Frere, 1995). Those enzymes belonging to classes A, B, and D are all serine-active-site enzymes that resemble serine proteases. During the reaction an acyl-enzyme intermediate is formed with the active site serine leading to the hydrolysis of the β-lactam antibiotics (Rahil and Pratt, 1991). Class B β-lactamases are distinct from the other three classes of β-lactamases. They are referred to as metallo-β-lactamases due to presence of at least one divalent metal ion in the active site for enzymatic activity (Ambler, 1980; Abraham and Waley, 1979). One or two zinc ions are present in all of the native metallo-β-lactamases isolated (Carfi et al, 1995; Concha et al., 1996).

An increasing number of bacteria are obtaining the gene structure necessary to produce β-lactamase, which makes them resistant to β-lactam antibiotics. Understanding the mechanism of hydrolysis of the β-lactam antibiotics is necessary for the production of new antibiotics and inhibitors (Abraham and Waley, 1979; Brenner and Knowles, 1984). For many years chemical alterations to existing β-lactam antibiotics have been used to stay ahead of drug resistance. In fact, cephalosporins have gone through four generations of this process (Maugh, 1981; Pitout et al., 1997). It has become increasingly common for a combination of inhibitor and antibiotic to be used to combat bacteria that are resistant. However, there are a limited number of alterations that can be made to the molecule and still maintain its bactericidal characteristics. The discovery of new classes of antibiotics and β-lactamase inhibitors is a costly and time-consuming process. For these reasons it is important to develop new β-lactamase inhibitors.

Combinatorial chemistry has become a commonly used technique for developing large numbers of possible ligands to target molecules. One technique involving the use of large pools of oligonucleotides for screening of functionality, which was independently developed in the labs of G. F. Joyce (La Jolla) (1989), J. W. Szostak (Boston) (Ellington, A. D. and Szostak, J. W., 1990), and L. Gold (Boulder) (Tuerk, C. and Gold, L, 1990). This technique is known as 'in vitro selection, 'in vitro evolution, or 'SELEX' (Systematic Evolution of Ligands by Exponential enrichment) all of which point to the evolutionary process of the selection. The functional molecules, called aptamers, can be separated from the non-functional molecules by a variety of separation techniques. This separation allows for the enrichment of the functional aptamers for the desired property. The functionalities of aptamers that have been discovered include the ability to bind to small organic molecules, to proteins that are known nucleotide binders, to proteins not known to bind nucleotides, and the alteration and development of ribozymes.

Figure 3:
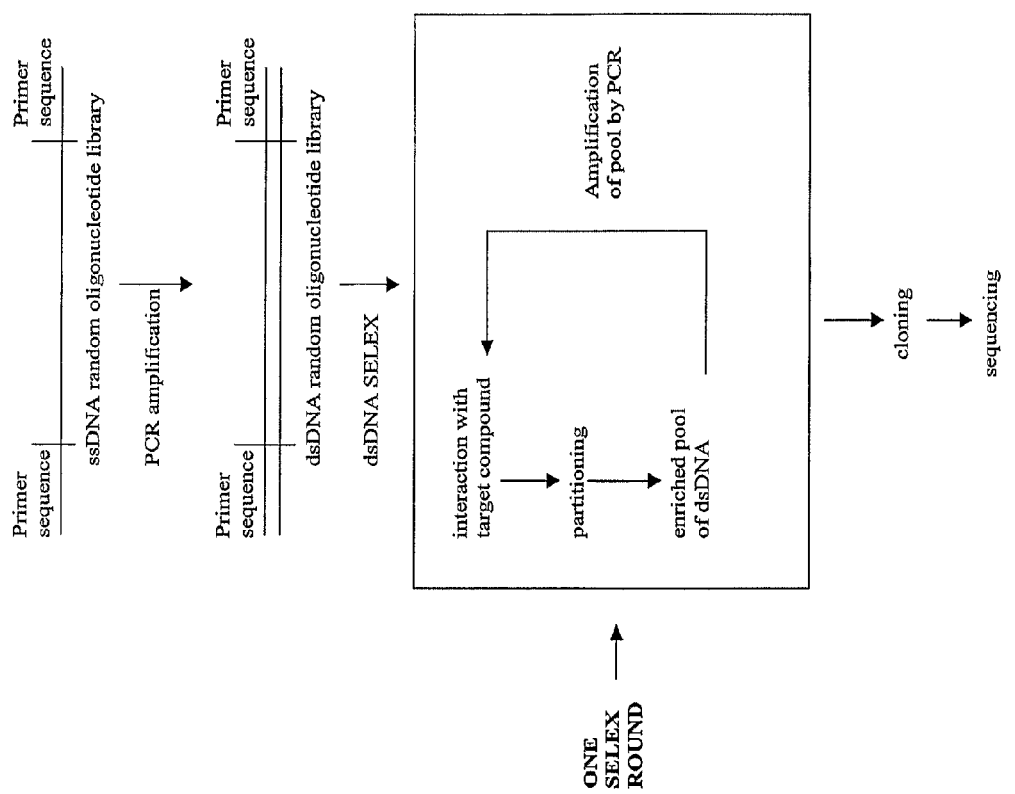

The starting pool of DNA for the technique is synthesized such that a random region in which each position may contain one of the four possible nucleotides. It is this region that brings in the complexity of the pool that generally ranges from 30 to 40 bases yielding up to $1.2 \times 10^{16}$ to $1.2 \times 10^{18}$ different sequences. This random region is flanked by two unique sequences that are used to amplify the DNA by PCR. Due to the tremendous number of different sequences that can be produced, which is much larger than the number of antibodies produced by mice, some of the sequences might have a desirable functionality. Very few of the aptamers present in the starting pool will have the desired functionality, so it is necessary to go through many successive selection and amplifications to obtain the desired aptamers (Klung and Famulok, 1994). Aptamers may consist of RNA, ssDNA, or dsDNA (FIG. 3) each of which follows similar procedures with unique steps pertaining to the type of aptamer being selected (Gold et al., 1995)

SUMMARY

Generally, this invention pertains to high affinity double stranded DNA molecules that specifically bind to metallo-β-lactamase. More specifically, the current invention involves relatively short high (14-29 base pair) double stranded high affinity ligands that inhibit an activity of Class B metallo-β-lactamase.

One aspect of the current invention is a composition. The composition is an isolated double stranded DNA molecule having a sequence that binds to a Class B metallo-β-lactamase under stringent conditions is described. In a preferred embodiment, a 29 base pair aptamer (29-mer) isolated double stranded DNA molecule is described and has a sequence that is at least 90% identical to SEQ ID No.: 4. However, shorter 14-mer and 15-mer versions of the 29-mer double stranded DNA are also useful. Each of the compositions are capable of binding a Class B metallo-β-lactamase that is at least 80% identical to SEQ ID No.: 8 or SEQ ID No.: 9, under stringent salt concentrations in the range of about 10 μM to about 50 μM NaCl.

A second aspect of the current invention comprises a method of identifying a target double stranded nucleic acid ligand that binds to a metallo-β-lactamase under stringent conditions. The method utilizes the following steps: (a) preparing a candidate mixture of nucleic acids, wherein the candidate mixture of nucleic acids comprise a pool of nucleic acid sequences having a region of about 30 to about 40 base pairs of random sequences flanked by two unique sequences that are used to amplify the DNA by PCR; (b) contacting the candidate mixture of nucleic acids with the metallo-β-lactamase, to form a candidate-enzyme mixture; (c) increasing the stringency of the candidate-enzyme mixture by the salt concentration and/or lowering the enzyme concentration to a predetermined values, wherein the target double stranded nucleic acid ligand has an increased affinity to the metallo-β-lactamase relative to the candidate mixture at the adjusted salt or enzyme salt concentrations, whereby the target double stranded nucleic acid ligand may be partitioned from the remainder of the candidate mixture; (d) partitioning the target double stranded nucleic acid ligand from the remainder of the candidate mixture; and (e) amplifying the target double stranded nucleic acid ligand to yield a pool of nucleic acid ligands enriched with the target double stranded nucleic acid ligand having a relatively higher affinity and specificity for binding to the metallo-β-lactamase, whereby the target double stranded nucleic acid ligand of the metallo-β-lactamase may be identified. The method can also repeat steps (c), (d), and (e) more than one additional round. Generally the candidate mixture comprises from about $1.2\times10^{16}$ to about $1.2\times10^{18}$ random candidate sequences. Another preferred embodiment includes enzymes very similar in amino acid sequence to the class B lactamase comprises a *B. anthracis* metallo-β-lactamase.

Figure 13:
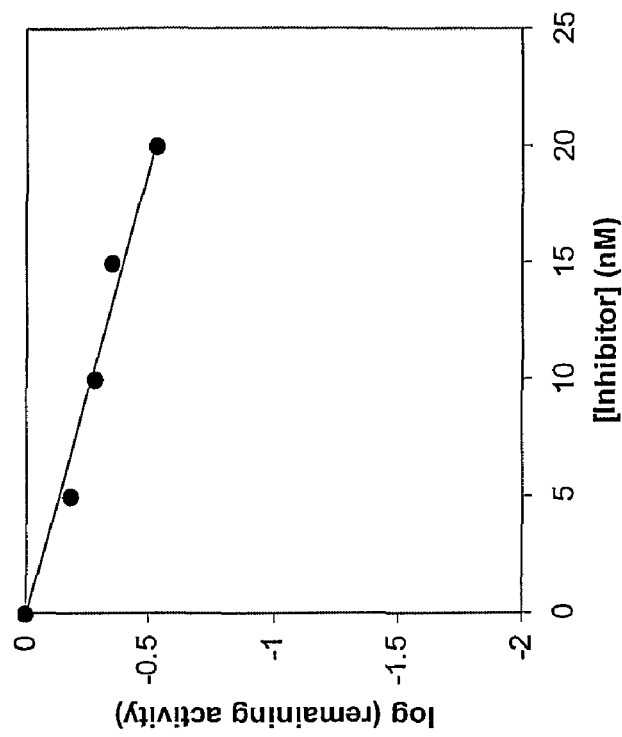
Figure 13:
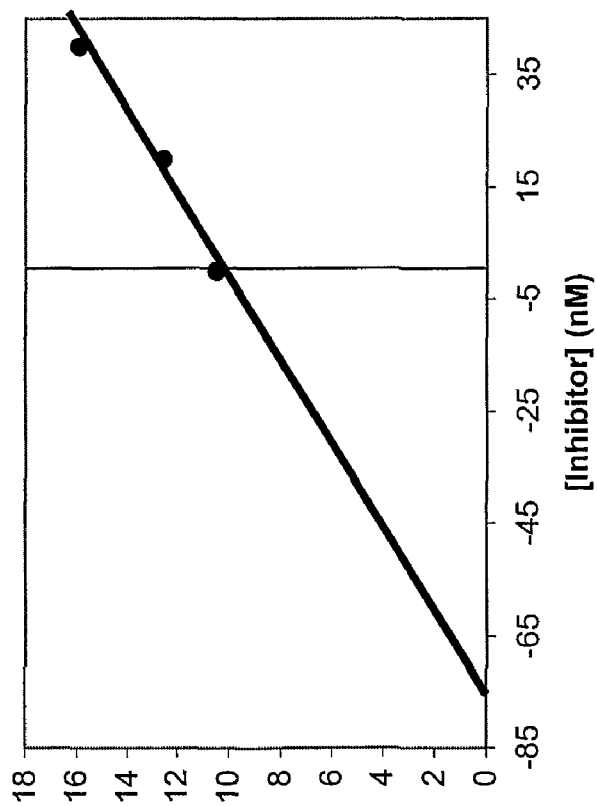

A third aspect of the current invention is a method of killing β-lactamase producing bacteria by delivering into the bacteria at least: (a) a β-lactam antibiotic; and (b) an isolated double stranded DNA molecule that is at least 90% identical to SEQ ID#4, which is capable of binding to a β-lactamase. In a preferred embodiment, the β-lactam antibiotic comprises a penicillin, a penicillin analog, cephalosporin, or a cephalosporin analog. The preferred method is utilized in β-lactamase producing bacteria such as: *Bacillus cereus; Bacillus anthracis; Bacillus fragillis; Escherichia coli; Bacteriodes; Staphlococcus epidermidis; Streptococcus; Psuedomonas aerugenosa; Providencia; Haemophilus; Xanthomonas maltophilia; Acinetobactor; Citrobactor, Enterobactor*, or *Branhamella*

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the structures of two general β-lactam antibiotics.

FIG. 2 shows catalysis of hydrolysis of generic β-lactam by a β-lactamase (Livermore, 1991).

FIG. 3 shows diagrammatic representation of the SELEX process (modified from Gold, et. al., 1995).

FIG. 4 shows determination of the IC50 for *B. cereus* metallo-β-lactamase by the 29-mer. The enzyme was incubated in the buffer (MOPS pH=7.0) for 15 minutes at 30° C. The concentration of the substrate (cephalosporin C) is 4 mM.

FIG. 5 shows a Lineweaver-Burk plot of the inhibition of *B. cereus* 5/B/6 metallo-β-lactamase the by 29-mer. Diamond: [I]=0 nM; Square: [I]=5 nM; Triangle: [I]=10 nM; Circle: [I]=15 nM. I=29-mer.

FIG. 6 shows a slope replot to estimate the $K_I$ of the 29-mer. Slope values $(K_M/V_{max})(1+([I]/K_I))$ for each inhibitor concentration from experimental data in FIG. 7 were determined using a non-linear regression computer program (Enzyme Kinetics, v. 1.2, Trinity software). Slope values were then plotted verses each of the corresponding inhibitor values. The x-axis intercept in this plot is $-K_I$.

FIG. 7 shows an intercept replot to estimate the $K_I'$ of the 29-mer. Intercept values $(1/V_{max})(1+([I]/K_I'))$ for each inhibitor concentration from experimental data in FIG. 7 were determined using a non-linear regression computer program (Enzyme Kinetics, v. 1.2, Trinity software). Intercept values were then plotted verses each of the corresponding inhibitor values. The x-axis intercept in this plot is $-K_I'$.

FIG. 8 shows a determination of the $IC_{50}$ for *B. cereus* metallo-β-lactamase by the 29-mer. The enzyme was incubated in the buffer (MOPS pH=7.0 and 1 mM $ZnSO_4$) for 15 minutes at 30° C. The concentration of the substrate (cephalosporin C) is 4 mM.

FIG. 9 shows determination of the time dependence of the 29-mer with metallo-β-lactamase. The enzyme was incubated with 10 nM 29-mer in buffer (50 mM MOPS) at 30° C. for the specified times.

FIG. 10 shows determination of the $IC_{50}$ for *B. cereus* metallo-β-lactamase by the 15-mer. The enzyme was incubated in the buffer (MOPS pH=7.0) for 15 minutes at 30° C. The concentration of the substrate (cephalosporin C) is 4 mM.

FIG. 11 shows a Lineweaver-Burk plot of the inhibition of *B. cereus* 5/B/6 metallo-β-lactamase the by 15-mer. Diamond: [I]=0 nM; Square: [I]=20 nM; Triangle: [I]=40 nM.

FIG. 12 shows a slope replot to estimate the $K_I$ of the 15-mer. Slope values $(K_M/V_{max})(1+([I]/K_I))$ for each inhibitor concentration from experimental data in FIG. 13 were determined using a non-linear regression computer program (Scientific Data Analysis Software, Version 1.1, Prentice Hall). Slope values were then plotted verses each of the corresponding inhibitor values. The x-axis intercept in this plot is $-K_I$.

FIG. 13 (A) shows a slope replot to estimate the $K_I'$ of the 15-mer. Slope values $(1/V_{max})(1+([I]/K_I'))$ for each inhibitor concentration from experimental data in FIG. 13 were determined using a non-linear regression computer program (Scientific Data Analysis Software, Version 1.1 Prentice Hall). Slope values were then plotted verses each of the corresponding inhibitor values. The x-axis intercept in this plot is $-K_I'$. FIG. 13 (B) shows a determination of the $IC_{50}$ for *B. cereus* metallo-β-lactamase by the 14-mer. The enzyme was incubated in the buffer (MOPS pH=7.0) for 15 minutes at 30° C. The concentration of the substrate (cephalosporin C) is 4 mM.

Figure 14:
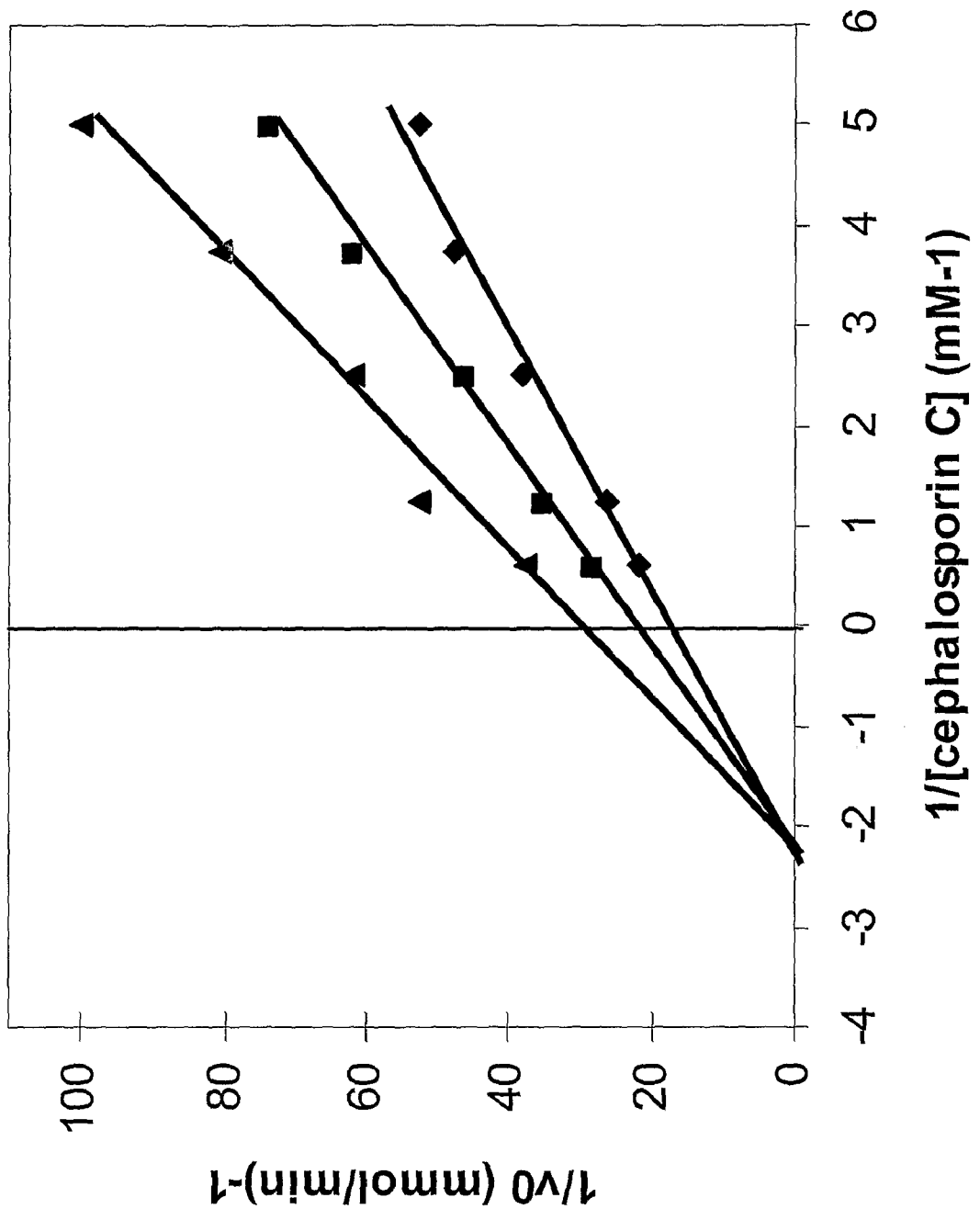

FIG. 14 shows a Lineweaver-Burk plot of the inhibition of *B. cereus* 5/B/6 metallo-β-lactamase the by 14-mer. Diamond: [I]=0 nM; Square: [I]=5 nM; Triangle: [I]=10 nM. I=14-mer.

Figure 15:
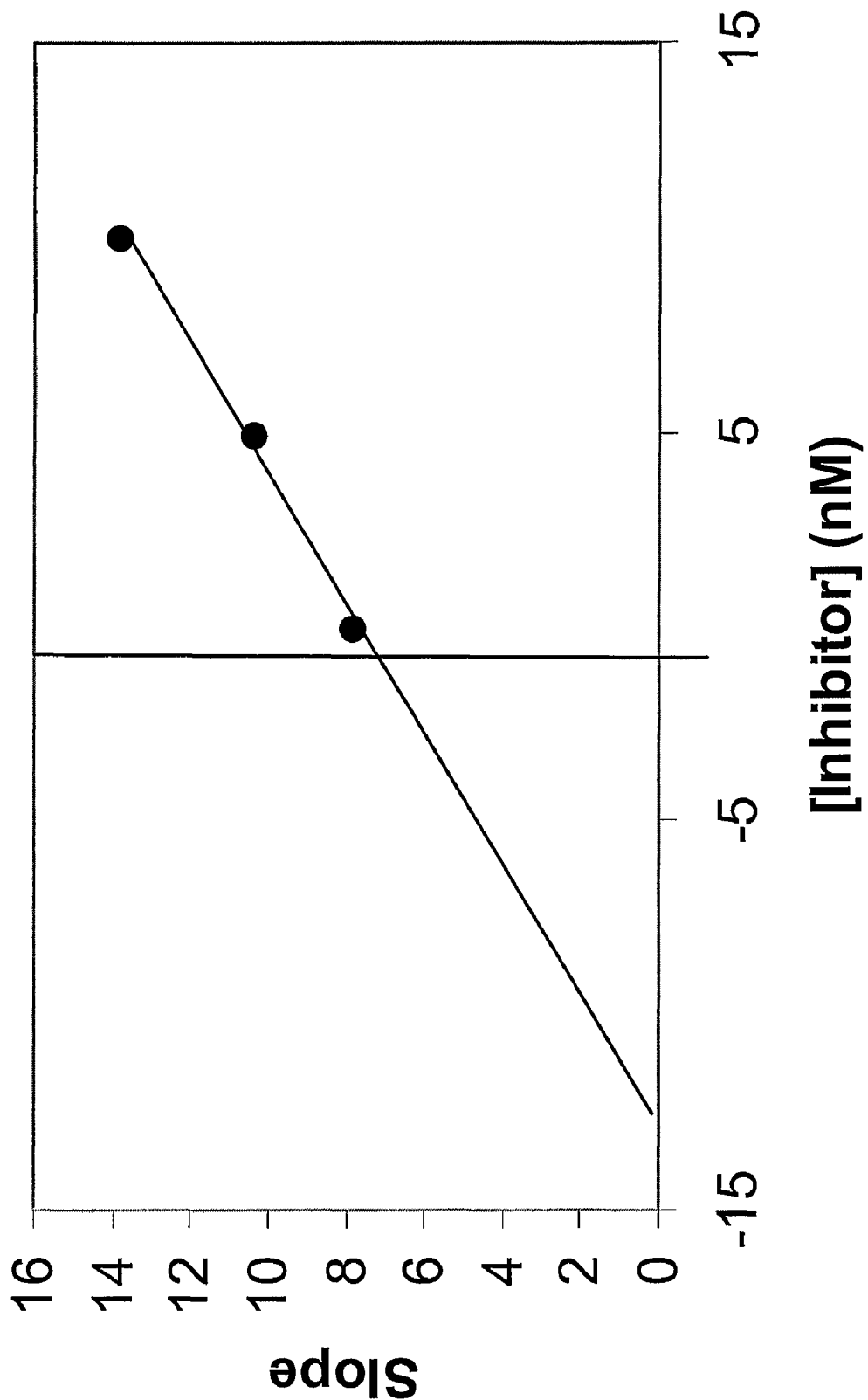

FIG. 15 shows a slope replot to estimate the $K_I$ of the 14-mer. Slope values $(K_M/V_{max})(1+([I]/K_I))$ for each inhibitor concentration from experimental data in FIG. 16 were determined using a non-linear regression computer program (Enzyme Kinetics, v. 1.2, Trinity software). Slope values were then plotted verses each of the corresponding inhibitor values. The x-axis intercept in this plot is $-K_I$.

Figure 16:
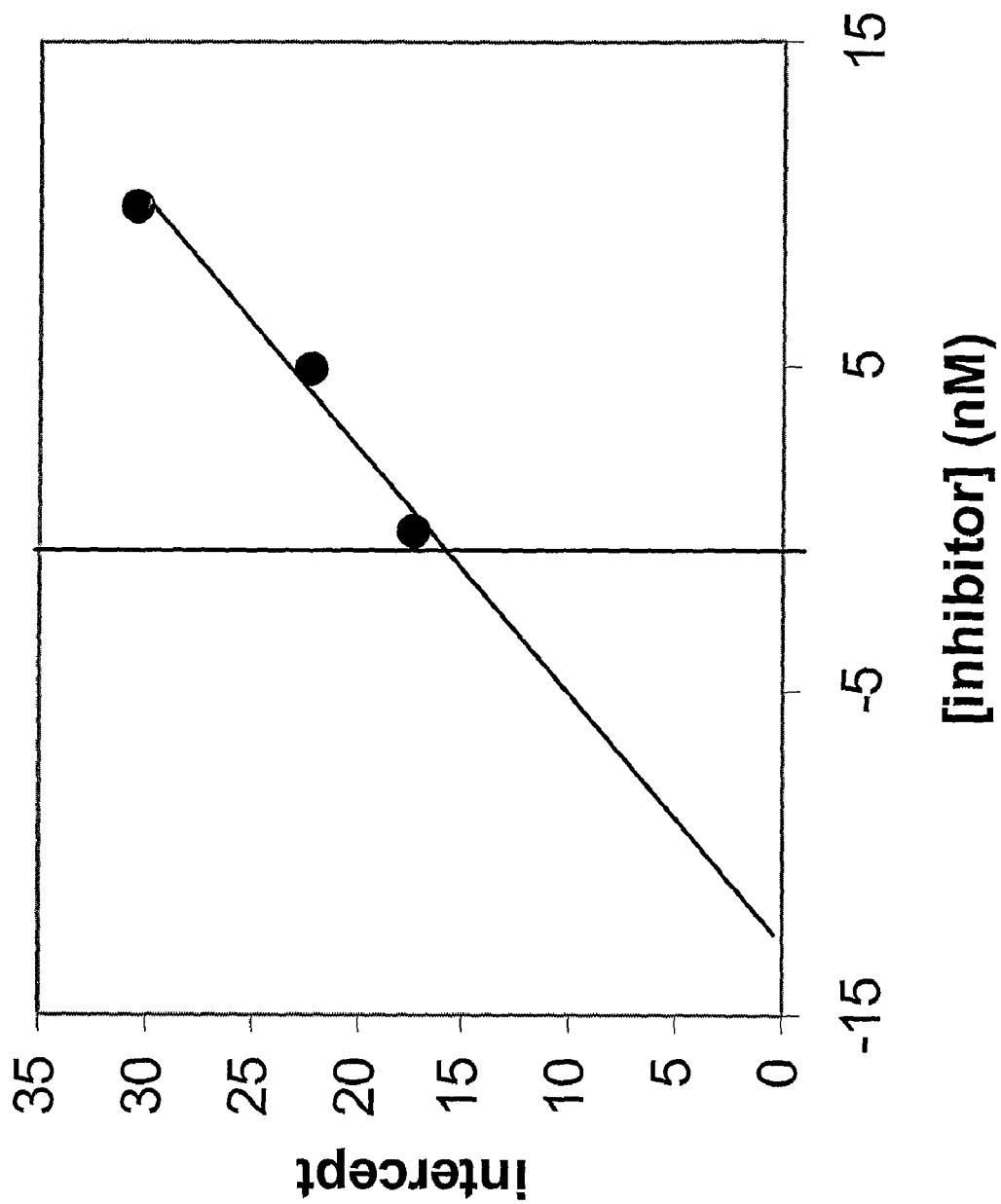

FIG. 16 shows an intercept replot to estimate the $K_I'$ of the 14-mer. Intercept values $(1/V_{max})(1+([I]/K_I'))$ for each inhibitor concentration from experimental data in FIG. 16 were determined using a non-linear regression computer program (Enzyme Kinetics, v. 1.2, Trinity software). Intercept values were then plotted verses each of the corresponding inhibitor values. The x-axis intercept in this plot is $-K_I'$.

Figure 17:
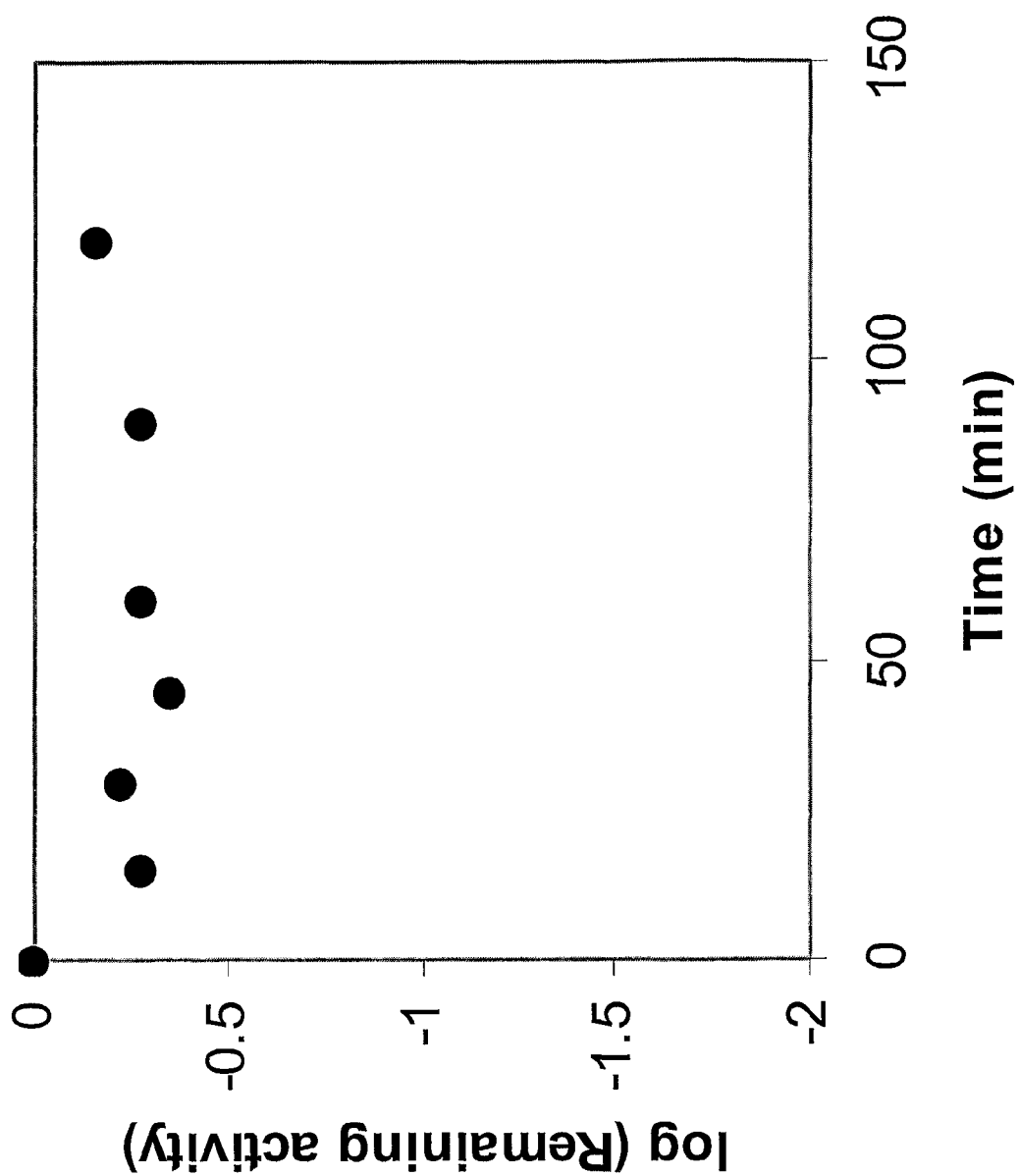

FIG. 17 shows determination of the time dependence of the 14-mer (SEQ ID No.: 6) with metallo-β-lactamase. The enzyme was incubated with 10 nM 14-mer in buffer (50 mM MOPS) at 30° C. for the specified times.

Figure 18:
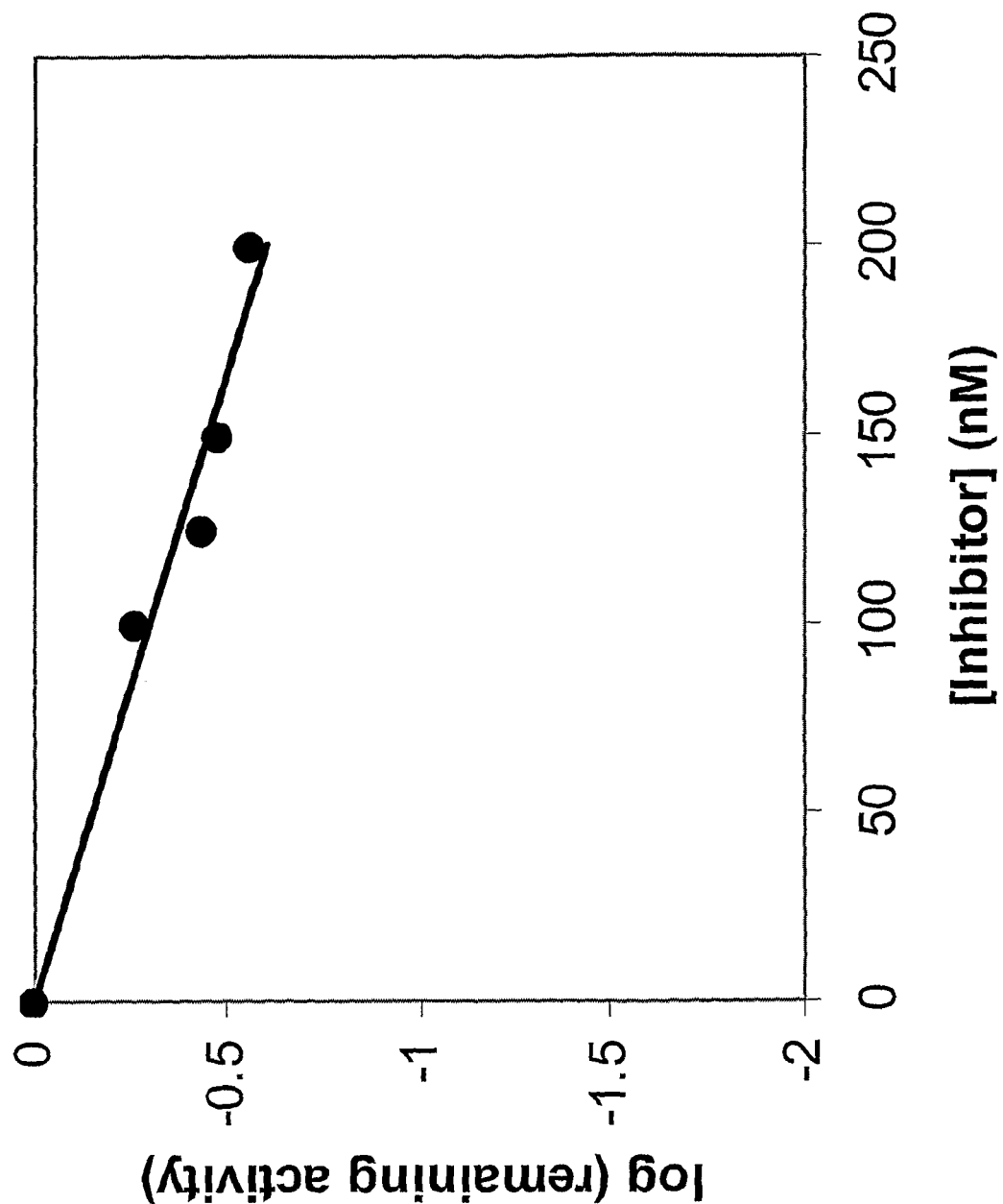

FIG. 18 shows the determination of the $IC_{50}$ for bovine carboxypeptidase A by the 14-mer. The enzyme was incubated in the buffer (10% LiC1) for 15 minutes at 30° C. The concentration of the substrate (Hippuryl-L-phenylalanine) is 1 mM.

FIG. 19 shows the double stranded 29-mer, 15-mer and 14-mer.

DETAILED DESCRIPTION OF PREFERRED EMBODIMENTS

Terms: It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "*B. cereus*" as used herein in the specification comprises *Bacillus cereus*.

The term "bp" as used herein in the specification may mean one or more base pairs.

The phrase "Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 15%, more typically less than 5%, and even more typically less than 1%) in an encoded sequence are "conservatively modified variations" where the alterations result in the substitution of an amino acid with a chemically similar amino acid. Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "ddH$_2$O" as used herein in the specification comprises distilled, deionized H$_2$O.

The term "DD-peptidases" as used herein in the specification may be one or more D-alanyl-D-alanine carboxypeptidases/transpeptidases.

The term "DE-MALDI-TOF MS" as used herein in the specification comprises Delayed Extraction Matrix Assisted Laser Desorption/Ionization Time Of Flight Mass Spectroscopy.

The term "dsDNA" as used herein in the specification is double stranded DNA.

The term "*E. coli*" as used herein in the specification comprises *Escherichia coli*.

The term "EDTA" as used herein in the specification comprises ethylenediamine tetraacetic acid.

The term "HEPES" as used herein in the specification comprises N-2-hydroxyethylpiperazine-N'-2-ethanesulfonic acid.

The term "IC$_{50}$" as used herein in the specification comprises an inhibitor concentration for 50% inhibition.

The term "K$_i$" as used herein in the specification comprises a dissociation constant of the enzyme-inhibitor complex.

The term "K$_i'$" as used herein in the specification comprises a dissociation constant of the enzyme-substrate-inhibitor complex The term "LB medium" as used herein in the specification comprises Lauria-Bertani Medium.

The term "MOPS" as used herein in the specification comprises 3-(N-morpholino) propanesulfonic acid.

The term "dNTP's" as used herein in the specification comprises deoxynucleotide triphosphates.

The term "PAGE" as used herein in the specification comprises polyacrylamide gel electrophoresis.

The term "PCI" as used herein in the specification comprises phenol:chloroform:isoamyl alcohol.

The term "PCR" as used herein in the specification comprises a polymerase chain reaction.

The terms "percentage of sequence identity" as used herein compares two optimally aligned sequences over a comparison window, wherein the portion of the sequence in the comparison window may comprise additions or deletions (i.e. "gaps") as compared to a reference sequence for optimal alignment of the two sequences being compared. The percentage identity is calculated by determining the number of positions at which the identical residue occurs in both sequences to yield the number of matched positions, dividing the number of matched positions by the total number of positions in the window and multiplying the result by 100 to yield the percentage of sequence identity. Total identity is then determined as the average identity over all of the windows that cover the complete query sequence. Although not wanting to be bound by theory, computer software packages such as GAP, BESTFIT, BLASTA, FASTA and TFASTA can also be utilized to determine sequence identity.

The term "pRE2" as used herein in the specification comprises a plasmid DNA expression vector.

The term "pRE2/bla" as used herein in the specification comprises a plasmid DNA expression vector containing the B. cereus 5/B/6 metallo-β-lactamase structural gene.

The term "SDS" as used herein in the specification comprises sodium docecyl sulfate.

The term "SELEX" as used herein in the specification comprises Systematic Evolution of Ligands by Exponential enrichment.

The term "ssDNA" as used herein in the specification comprises single stranded DNA.

The term "TEMED" as used herein in the specification comprises N,N,N',N'-tetra-methylethylenediamine.

The term "TA" as used herein in the specification comprises 20 mM Tris (pH=7.0) and 20 mM acetic acid.

The term "TE" as used herein in the specification comprises 10 mM Tris (pH=7.0) and 1 mM EDTA.

The term "Tris" as used herein in the specification comprises 2-amino-2-(hydroxy-methyl)-1,3-propanediol.

The term "UV" as used herein in the specification comprises ultraviolet.

The term "V" as used herein in the specification comprises volts.

The term "identical" in the context of two nucleic acid or polypeptide sequences refers to the residues in the two sequences that are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a fill mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11-17 (1988); Smith and Waterman (1981) Adv. Appl. Math. 2: 482; Needleman and Wunsch (1970) J. Mol. Biol. 48: 443; Pearson and Lipman (1988) Proc. Natl. Acad. Sci. USA 85: 2444; Higgins and Sharp (1988) Gene, 73: 237-244 and Higgins and Sharp (1989) CABIOS 5: 151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31. Alignment is also often performed by inspection and manual alignment.

The term "isolated" as used herein refers to synthetic or recombinant preparation of molecules in a purified, or concentrated, or both, form, substantially free from undesirable properties.

Materials and Methods. The following description of preferred materials and methods are provided to demonstrate the manner in which the invention may be carried out. However, it is understood that the specific details of materials or methods have been chosen for purposes of illustration only and not be construed as limiting the invention or the methods of producing or analyzing specific materials described herein.

Metallo-β-lactamase. Escherichia. coli MZ1 carrying the plasmid pRE2/bla was used in the production of the metallo-β-lactamase from B. cereus 5/B/6 and was purified according to the procedures described previously (Shaw et al., 1991). Purity of the enzyme was determined by specific activity, native and SDS PAGE, and DE-MALDI-TOF. DEAE Sephacel, CM Sepharose CL-6B, Sephadex G-25 (superfine) and various columns were purchased from Pharmacia or Bio-Rad Laboratories (Richmond, Calif.). Synthetic oligonucleotides used in SELEX were synthesized using a Beckman (Fullerton, Calif.) Oligo 1000M oligonucleotide synthesizer. PCR reactions were carried out using a Perkin Elmer (Wellesey, Mass.) Certus Thermocycler. Automated DNA sequencing was performed on an ABI PRISM™ 310 Genetic Analyzer from Applied Biosystems Inc. (Foster City, Calif.). Klenow, restriction endonucleases NdeI and SacI were purchased from New England Biolabs, Inc. (Ipswich, Mass.), and used according to manufacture's recommendations. Pfu polymerase was purchased from Stragene (La Jolla, Calif.). T4 DNA ligase was purchased from Promega (Madison, Wis.). The Gene Clean II Kit was purchased from Qbiogene (irvine, Calif.). PCI (Phenol:Chloroform:Isoamyl alcohol; 25:24:1) and electrophoresis grade agarose were purchased from Amresco (Solon, Ohio). PCR 20 bp low ladder, ethidium bromide, dimethysulfoxide (DMSO), acrylamide, bisacrylamide, benzylpenicillin, cephalosporin C (potassium salt), ampicillin, cesium chloride, EDTA, glucose, sodium hydroxide, potassium hydroxide, rubidium chloride, MOPS, Tris, $ZnSO_4$, and various other inorganic salts were obtained from Sigma Chemical Co. (St Louis, Mo.). Bacto-agar, casamino acids, and yeast extract were used to make all media and plates were obtained from Fisher Scientific (Hampton, N.H.).

SELEX Method: Oligonucleotides were synthesized using a Beckman Instruments, Inc. (Fullerton, Calif.) OLIGO 1000M DNA synthesizer. The oligonucleotide consisted of 61 bases including a 30 base random region flanked by two unique primer sequences. Each of the primers contained a unique restriction enzyme site of either SacI or NdeI for future cloning.

```
61 mer:
                                              (SEQ ID No.: 1)
5'CGCGAGCTCCGCGCG(N)30CGCGCGCATATGGCGC 3'
      SacI                      NdeI
dsDNA was produced from this template by either
Klenow method (Brown, 1998).

5' Primer (16 mer) containing the NdeI restriction
site:
                                              (SEQ ID No.: 2)
5'GCGCCATATGCGCGCG3'

3' Primer (15 mer) containing the SacI restriction
site:
                                              (SEQ ID No.: 3)
5'CGCGAGCTCCGCGCG3'
Klenow.
```

The initial starting dsDNA pool was produced using the Klenow method (Brown, 1998) for second strand synthesis. Annealing of the ssDNA and 5' primer occurred in a solution containing 50 μmol of 61 mer, 150 μmol of 5' primer, 50 μl of 1M NaCl, 2.5 μl 1M Tris-HCl buffer (pH 7.5) to a volume of 100 μl. This solution was placed at 92° C. for 1 minute and then allowed to cool to 25° C. In order to precipitate the DNA, 2 volumes of cold ethanol (EtOH) was added and the solution was placed at −20° C. for 1 hour, −80° C. for 15 minutes, centrifuged for 15 minutes at 25° C., and dried for 15 minutes in a heated vacuum centrifuge. This pellet was then dissolved in 5.5 μl of ddH$_2$O to which was added 2.5 μl of 2 mM dNTPs, 1 μl of buffer (200 mM HEPES/NaOH (pH 6.9), 140 mM KCl, 20 mM MgCl$_2$, 5 mM DTT), 1 μl (5 units (One unit is the amount of enzyme required to convert 10 nmoles of dNTPs to an acid insoluble form in 30 min at 37° C.)) Klenow (large fragment of DNA polymerase I) and incubated at room temperature. An additional 1 μl of Klenow was added to the solution after 1 hour. After an additional hour, 190 μl of Tris-EDTA (TE) buffer was added to stop the reaction. Removal of the Klenow enzyme was carried out by adding an equal volume of phenol:chloroform:isoamyl alcohol (25:24:1). This was vortexed for 1 minute followed by centrifugation for 1 minute. The top phase of the solution was retained and treated with chloroform:isomyl alcohol (24:1), vortexed for 1 minute, and centrifuged for 1 minute. The top phase of the solution was retained and a 10% volume of sodium acetate (pH 3.8) was added followed by 2 volumes of EtOH. This solution was placed at −20° C. for 1 hour, −80° C. for 15 minutes, centrifuged for 25 minutes at 4° C., washed with 70% EtOH, and dried for 15 minutes in a heated vacuum centrifuge.

Desalting of Enzyme. The stock enzyme solution contained 150 mM ammonium sulfate, 10 mM sodium citrate (pH=7.0), 1 mM zinc sulfate, and 30% glycerol (v/v) all of which were removed by gel filtration. Due to the stability of the enzyme at 60° C., the solution was placed in a water bath for 30 minutes at that temperature to remove any trace contaminating proteins. The sample was then centrifuged for 1 minute and the pellet, if any, was discarded and the supernatant was recovered. Removal of the ammonium sulfate, sodium citrate, and glycerol was necessary to decrease the ionic strength of SELEX incubation solution. This was accomplished by passing the solution through a Sephadex G25 (superfine) column (15 cm×1 cm) in a 50 mM MOPS/1 mM ZnSO$_4$ buffer (pH=7.0). Fractions were then monitored spectrophotometrically at 280 nm to determine which contained protein. An activity assay using these samples was performed to identify the presence of the enzyme. This sample was then concentrated by ultrafiltration using a 23 mm Amicon YM-10 membrane. Determination of the concentration of the sample was accomplished by the Lowery method (Lowery et al., 1951) and an activity assay was performed as well.

Gel Shift Assay. An electrophilic mobility shift assay used 6% (w/v) polyacrylamide (29:1 mono:bis) in 20 mM Tris-acetate (TA) buffer (pH=7.0), polymerized with 0.07% (v/v) ammonium persulfate, and 0.0028% (v/v) TEMED. The desalted enzyme from the above procedure was diluted in a dilution buffer (20 mM Tris and 1 mM ZnSO$_4$, pH=7.0). dsDNA from the previously mentioned Klenow reaction or PCR products were incubated with the enzyme for separation of functional aptamers. The incubation buffer included 20 mM Tris buffer (pH=7.0), 1 mM ZnSO$_4$, NaCl depending on the cycle of SELEX, enzyme, and dsDNA in a total volume of 20 ml was placed at 30° C. for 15 minutes. Beginning with the 6th round the buffer was changed to 20 mM TA buffer. Enzyme and NaCl concentrations in the incubation solution were adjusted to increase stringency of binding through the progression of the rounds of SELEX. At the end of 15 minutes 40% (v/v) glycerol was added to the solution to give a 10% (v/v) final glycerol concentration to increase the density of the sample for gel loading. This sample was then run on a 6% (w/v) polyacrylamide gel at 200 V for 35-40 minutes.

Separation of the dsDNA:enzyme complex from unbound dsDNA was accomplished on the 6% acrylamide gel mentioned above. The gel was then soaked in the 70 mL of the 20 mM TA buffer and 5 μL (1 mg/100 mL) ethidium bromide. Destaining for 10 minutes in ddH$_2$O followed staining of the gel. Visualization of the dsDNA:enzyme complex by UV light using a TM-36 chromato-UVE transilluminator by UVP Inc. The DNA-enzyme complex was excised using a razor blade.

Generation of double-stranded DNA by PCR. The following PCR method (modified from the Stragene method) was used in the production of the dsDNA pool to be used in successive SELEX rounds. The excised band from above was then cut into several pieces; each piece placed in a separate 250 ml PCR tube, and crushed using a disposable pipette tip. A solution containing 2.5 units of pfu polymerase, 200 ng of 5' primer (16 mer), 200 ng of 3' primer, 0.2 mM dNTPs, and 10 μl of 10×pfu buffer for a final reaction volume of 100 μl. This was then subjected to 3 minutes at 95° C. and then 30 cycles of 45 seconds at 95° C., 45 seconds at 55° C., and 6 seconds at 72° C. followed by 10 minutes at 72° C. for final extension of all primers.

Purification of the PCR product was performed using a 12% (w/v) polyacrylamide gel (29:1 mono:bis). Conformation of the correct 61 base pair size was performed by comparison of size using a 20 bp ladder standard DNA size marker (Sigma). The correct band size was then excised using a razor blade and placed in a microcentrifuge tube. dsDNA was then extracted using a modified crush and soak method (Maxam and Gilbert, 1977) with the following changes: Each tube was weighed to determine the volume of the polyacrylamide and 1-2 volumes of elution buffer (0.5 M ammonium acetate, 1 mM EDTA (pH=8.0) and 0.1% (w/v) SDS) were added. This solution was then incubated at 45° C. for 2.5-3 hours on a rotary platform. The tube as then centrifuged at 12,000 g for 1 minute and the supernatant was transferred to a new microcentrifuge tube. The polyacrylamide fragments were filtered out using glass wool. Then ½ volume of elution buffer was added to the original microcentrifuge tube, vortexed, and recentrifuged. This slurry was then placed in the plastic column and centrifuged for 15 seconds to pass the supernatant into the new microcentrifuge tube. Then 2-2.5 volumes of cold 100% ethanol was then added to the tube and placed at −20° C. for 1 hour, −80° C. for 15 minutes, centrifuged at 4° C. for 25 minutes, and then dried. The ethanol precipitation aided in the removal of the ethidium bromide so that the dsDNA could reassume its original solution structure.

Cloning and Sequencing. Plasmid pRE2/bla was digested with restriction endonucleases SacI and Nde I (Reddy, Peterkofsky, and McKenney, 1989). The double digested products were separated on a 1% (w/v) agarose gel in TBE buffer at 60 V for 3 hours. The gel was then stained with 5 μg/mL of ethidium bromide for the visualization of the linear pRE2 vector and metallo-β-lactamase gene fragments by UV. These linear fragments were removed from the gel and purified using the Gene Clean II kit.

PCR amplification of the SELEX product was performed from the previous SELEX round. An ethanol precipitation was performed and then the products' fixed regions were digested with the restriction endonucleases SacI and NdeI.

The products were then run on a 12% (w/v) polyacrylamide gel (29:1 mono:bis) and then purified by the modified crush and soak method.

Ligation of the fragments with the linear pRE2 fragment was achieved using T4 DNA ligase at 4° C. overnight. The ligation reaction consisted of 300 ng of linear pRE2, 1 ng of linear fragment, 3 units of T4 DNA ligase and buffer to a final volume of 10 μL. The mixture was then used to transform $E.$ $coli$ strain Tap 56 competent cells prepared by the Hanahan method (Hanahan, 1983). The transformed cells were then grown for 4-5 hours at 30° C. and then transferred to LB medium of 1% (w/v) casamino acids, 0.5% (w/v) yeast extract, 0.5% (w/v) sodium chloride (pH=7.0, adjusted with 3 M NaOH) and 50 μL/mL of ampicillin. This culture was then grown overnight at 30° C. with gentle shaking. The resulting subcloned plasmid DNA was then prepared using the boiling miniprep method (Sambrook et al., 1989). The subsequent DNA plasmid that was extracted by the boiling miniprep method was then sequenced using an ABI PRISM™ 310 genetic analyzer. The 29-mer insert that was found by sequencing was then synthesized using a Beckman Instruments Inc. OLIGO 1000M DNA synthesizer. dsDNA of this synthesized oligonucleotide was used in the remaining experiments.

Annealing of 15-mer and 14-mer. Smaller subfragments of the original aptamer produced improved inhibition kinetics compared to the original aptamer. The smaller aptamer was chosen based on secondary structure calculations (using M-fold) on the aptamer, which suggested the formation of a stem and loop structure. We assume that the double-stranded 29-mer is a double helix throughout its sequence. Therefore, the molecule was divided into half to produce two subfragments, a 15-mer and a 14 mer (as shown in FIG. 21).

The two subfragments of the 29-mer final product from the SELEX experiments were synthesized and in order to test their ability to inhibit the metallo-β-lactamase. Complementary strands of each of the oligonucleotides were synthesized using a Beckman Instruments, Inc. OLIGO 1000M DNA synthesizer. Annealing of each of the sets of DNA fragments was carried out in a buffer of 0.01 M Tris (pH=7.5), 50 μM NaCl, and 1 mM EDTA to which 10 mmol of each complementary strand was added. The solution was heated to 94° C. for 2 minutes and allowed to cool for 45 minutes. Two volumes of cold 100% ethanol was then added to the tube and placed at −20° C. for 1 hour, −80° C. for 15 minutes, centrifuged at 4° C. for 25 minutes, and dried.

Purification of the PCR product was performed using a 12% (w/v) polyacrylamide gel (29:1 mono:bis). Confirmation of the correct 14 or 15 base pair size was performed by comparison of size using a 20 bp ladder. The correct band size was then excised using a razor blade and placed in a microcentrifuge tube. dsDNA was then extracted using a modified crush and soak method (Maxam and Gilbert, 1977) with the following modifications: Each tube was weighed to determine the volume of the polyacrylamide and 1-2 volumes of elution buffer (0.5 M ammonium acetate, 1 mM EDTA (pH=8.0) and 0.1% (w/v) SDS) were added. This solution was then incubated at 45° C. for 2.5-3 hours on a rotary platform. The tube as then centrifuged at 12,000 g for 1 minute and the supernatant was transferred to a new microcentrifuge tube. The polyacrylamide fragments were filtered out using glass wool. Then ½ volume of elution buffer was added to the original microcentrifuge tube, vortexed, and recentrifuged. This slurry was then placed in the plastic column and centrifuged for 15 seconds to pass the supernatant into the new microcentrifuge tube. Then 2-2.5 volumes of cold 100% ethanol was then added to the tube and placed at −20° C. for 1 hour, −80° C. for 15 minutes, centrifuged at 4° C. for 25 minutes, and dried. The ethanol precipitation aided in the removal of the ethidium bromide so that the dsDNA could reassume its original structure.

β-lactamase I Assay. The assay used for the β-lactamase I assay is based on the method developed by Davies et al. (1974) with some modifications. The enzyme sample with or without inhibitor was incubated with 20 mM EDTA (pH=7.0) at 30° C. for 15 minutes prior to the assay. The enzymatic hydrolysis of 1.1 mM benzylpenicillin in 50 mM MOPS (pH=7.0) and 1 mM EDTA was continuously monitored at 231 nm at 30° C.

Bovine Carboxypeptidase A Assay. The assay used for the bovine carboxypeptidase A is based on the method developed by Folk and Schirmer (1963). The rate of hydrolysis of hippuryl-L-phenylalanine is determined by monitoring the increase in absorbance at 254 nm (25° C., pH=7.5). The enzyme was dissolved in 10% lithium chloride to a concentration of 1-3 units per mL. Hippuryl-L-phenylalanine (1 mM) was dissolved in 0.05 M Tris HCl, pH=7.5 with 0.5 M sodium chloride. In a 1 cm cuvette, 1.0 mL of substrate was added and incubated in the spectraphotometer at 25° C. for 3-4 minutes to reach temperature equilibrium and establish a blank rate. Fifty μL of diluted enzyme was preincubated for 15 minutes at 25° C. with or without the inhibitor and was then added to record the increase in absorbance at 254 nm.

EXAMPLES

The following examples are provided to further illustrate this invention and the manner in which it may be carried out. It will be understood, however, that the specific details given in the examples have been chosen for purposes of illustration only and not be construed as limiting the invention.

Example 1

The 29-mer (SEQ ID No.4). A rational drug design approach to the inhibition of class A & B β-lactamases was utilized in order to produce inhibitors for β-lactamase (Buynak et al., 2004). Additionally, a combinatorial chemistry method approach of SELEX was utilized to test many different molecules for a specific functionality. This resulted in the production of high affinity inhibitors for the (class B) metallo-β-lactamase.

Figure 4:
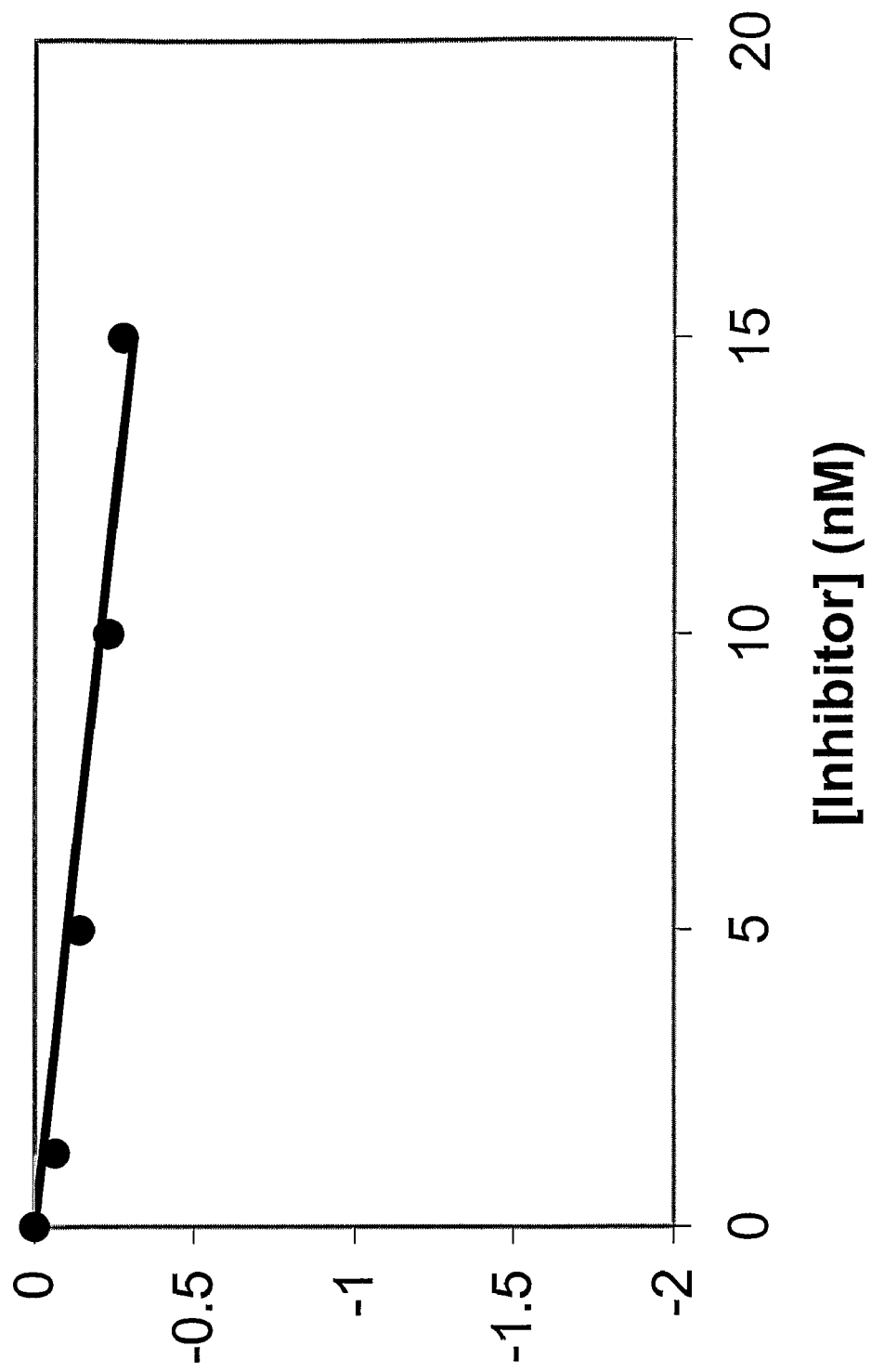

Initially a 61 base pair single-stranded synthetically produced oligonucleotide was produced by Klenow second strand synthesis, as shown in FIG. 4 and SEQ ID No.:1. The small size of the double-stranded product required the use of a polyacrylamide gel instead of an agarose gel. Following separation of the PCR products, the correct sized oligonucleotides were recovered and used for the SELEX experiments. A modified crush and soak method was used to isolate enough purified DNA to be used for the SELEX experiments with additional back-up material (Maxam and Gilbert, 1997).

The 61-mer dsDNA (SEQ ID No.:4) was incubated with a desalted enzyme to form a dsDNA:enzyme complex. The dsDNA:enzyme complex was separated from free dsDNA by electrophoresis. An electrophilic mobility assay was utilized to separate the bound DNA from the unbound DNA. This method takes advantage of the difference in overall charge and size of our protein. For example, due to the positive charge of metallo-β-lactamase, the enzyme does not migrate in the same direction as a negatively charged dsDNA molecule. However, any dsDNA that forms a complex metallo-β-lactamase also changes the electric properties of the entire complex and allows the dsDNA:enzyme complex to migrate into the gel in the same direction as the unbound dsDNA. The dsDNA: enzyme complex can then be visualized using various staining procedures that are commonly known in the art, (e.g. ethidium bromide for DNA and Coomassie blue R250 for proteins). The large size of the dsDNA:enzyme complex also provides good separation from the unbound DNA. To demonstrate that the dsDNA used in the experiments had a specific number of base pairs, the PCR product visualized on a 12% polyacrylamide gel and compared with a 20 base pair ladder. The product of a predetermined length was excised and purified by a crush and soak method before incubation with the target enzyme. In order to decrease the initial stringency of the binding, the enzyme was desalted.

The existence of the dsDNA:enzyme complex was visualized using an ethidium bromide stain for DNA and Coomassie Blue 250 stain for protein (data not shown). The separation of dsDNA: enzyme complex from free dsDNA by electrophoresis allowed for the visualization the complex as a band after in each round of SELEX. However, the knowledge of the approximant location of the complex in the gel is useful during the later rounds of SELEX because it can be difficult sometimes to visualize the complex in ethidium bromide stained gels due to low enzyme concentrations. The band of dsDNA:enzyme complex was excised and amplified using PCR. The resulting PCR products were then separated using electrophoresis on a 12% gel having a 20 base pair ladder for comparison. This process was repeated for each successive round of SELEX.

This stepwise method was advantageous because the stringency could be controlled during each successive round of SELEX and the conditions for the next round could be readily determined. For example, during the first few rounds of SELEX, the salt concentration was increased initially and the enzyme concentration gradually decreased. However, beginning with round 8, the salt was removed from the incubation buffer and the enzyme concentration was steadily decreased in each round.

Control of the stringency of binding was useful in order to decrease the nonspecific binding of oligonucleotides to the enzyme. Increasing the stringency of the binding was achieved by decreasing the concentration of the enzyme present in the incubation. This can be done gradually so as not to cause a rapid loss in bound dsDNA, which would result in a complex that is difficult to visualize using an ethidium bromide stain for DNA. Increasing the concentration of salt in the incubation buffer also allowed for increased stringency. However, increased salt can lead to an increase in the conductance of the gel, which causes bands to smear and/or making visualization of the location of the complex more difficult. Therefore, in a preferred embodiment, the salt was removed from the incubations and decreasing the enzyme concentration was utilized to provide the stringency.

The ability of the aptamers pool to inhibit the metallo-β-lactamase was checked after round 8. This preliminary inhibition test is not extremely accurate because of the method used for quantitation of the dsDNA (comparison of relative fluorescence intensity by comparison to a standard on a gel stained with ethidium bromide). Round 8 resulted in 25% inhibition of the enzyme. Four additional rounds of SELEX were carried out. The product of round 12 was subcloned into the pRE2 vector, which was then sequenced. This resulted in a single sequence, which contained 29 bases instead of the original 30-nucleotide insert. The sequence is shown in SEQ ID No.:4:

(SEQ ID No.: 4)
5'-(dATGATCCGGTGCTGTATGTTCCTACATGA)-3'.

Although not wanting to be bound by theory, due to the use of PCR in the production of the random pool after each round, it is possible that a primer mismatch occurred resulting in the loss of one base (Baker and Rothberg, 1998). The loss of one nucleotide during a single PCR experiment would not be a factor since it would not produce DNA molecules to be the major component of the product. Although not wanting to be bound by theory, the separation of DNA with only one base pair difference is difficult without the use of fluorescent dyes such as those used in sequencing. However, due to the evolutionary basis of the method and the selection of high affinity molecules this sequence could be maintained and amplified in subsequent PCR cycles.

Since round 12 resulted in a single sequence (29-mer aptamer), it was synthesized using a Beckman Oligo 1000M oligonucleotide synthesizer. The double stranded form of this resultant synthetic oligonucleotide was tested for its ability to inhibit the activity of two different enzymes: $B.\ cereus$ 569/H/9 β-lactamase I; and zinc-dependent bovine carboxypeptidase A. The activity of each enzyme was tested in the presence of the 29-mer.

Inhibition assays. The class A β-lactamase I enzyme was chosen to determine whether competition for the substrate binding site was involved in the inhibition. The lack of inhibition of this enzyme indicates that the specificity of the 29-mer is not related solely to the substrate-binding site. This is also consistent with the noncompetitive inhibition pattern obtained in the steady state kinetics experiments. Zinc-dependent bovine carboxypeptidase A was chosen based on the similarities noted between carboxypeptidase A and the metallo-β-lactamase in both structure ($Zn^{2+}$ dependence), mechanism of reaction, and inhibition by EDTA (Alberts et al., 1998; Bouagu et al., 1998). The lack of inhibition of bovine carboxypeptidase A suggests that if indeed the metal ion(s) is (are) complexed by the inhibitor, the chelation is not indiscriminate as one finds in both EDTA and 2-mercaptoethanol.

The $IC_{50}$ value for the 12th round 29-mer aptamer was determined by measuring the enzymatic rate of hydrolysis of cephalosporin C following preincubation and assay in varying concentrations of the 29-mer. This resulted in an $IC_{50}$ of 14 nM for the 29-mer (FIG. 4). An $IC_{50}$ value of 14 nM can be considered an impressive value when compared to other known inhibitors of metallo-β-lactamase (Payne et al., 1997, Yang and Crowder, 1999, Scrofani et al, 1999, Mollard et al., 2001).

Figure 5:
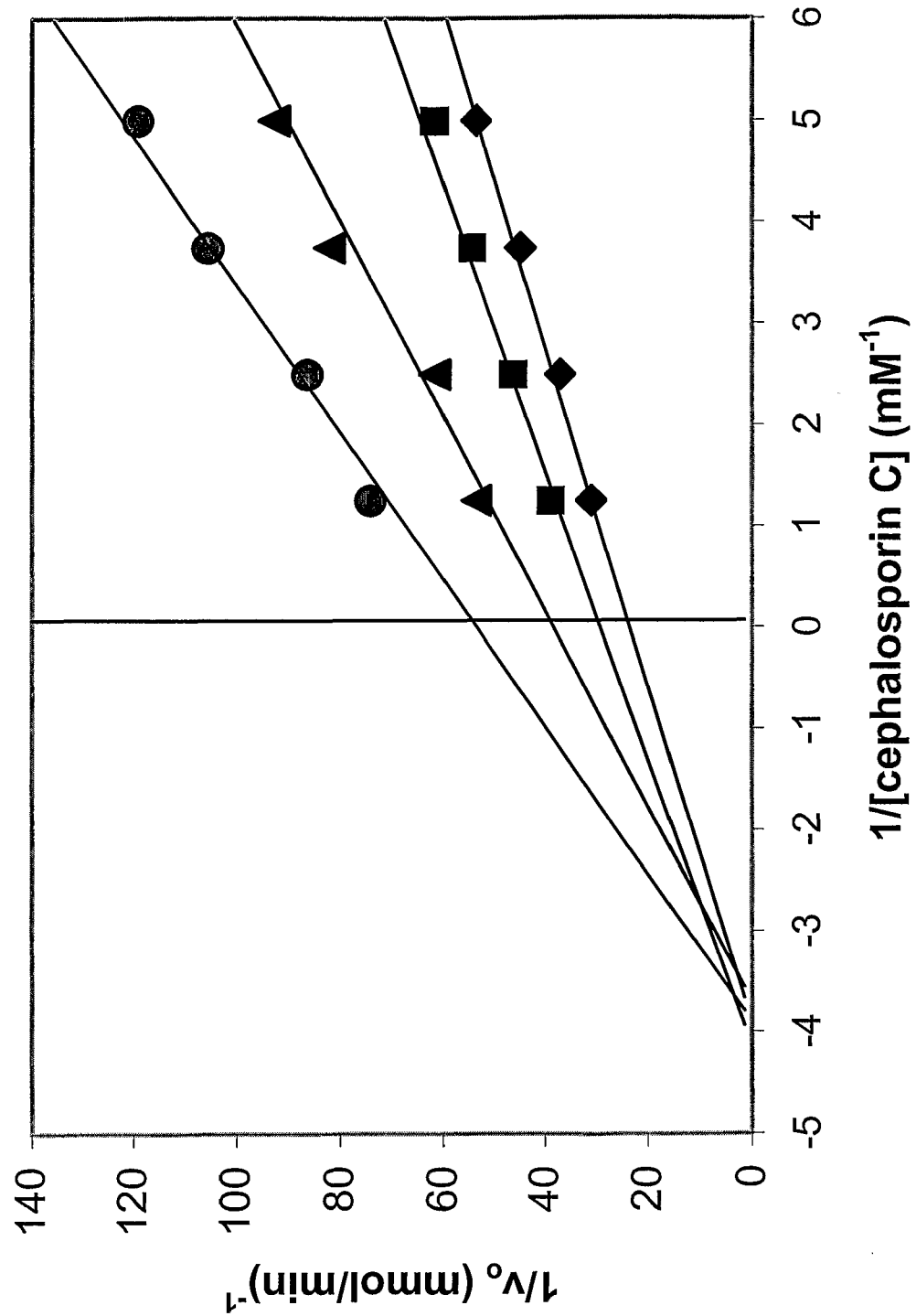

A steady-state kinetic study of the 29-mer was performed, resulting in a noncompetitive inhibition pattern of the enzyme as shown in FIG. 5. FIG. 5 shows a Lineweaver-Burk plot of the inhibition of $B.\ cereus$ 5/B/6 metallo-β-lactamase the by 29-mer (Diamond: [I]=0 nM; Square: [I]=5 nM; Triangle: [I]=10 nM; Circle: [I]=15 nM. I=29-mer). Replots of the slope and intercept gave a $K_i$ value (dissociation constant for the inhibitor from the enzyme-inhibitor complex) for the 29-mer of 11 nM (as shown in FIG. 6) and the value (dissociation constant for the inhibitor from the enzyme-substrate-inhibitor complex) of 9.1 nM (as shown in FIG. 7).

Figure 6:
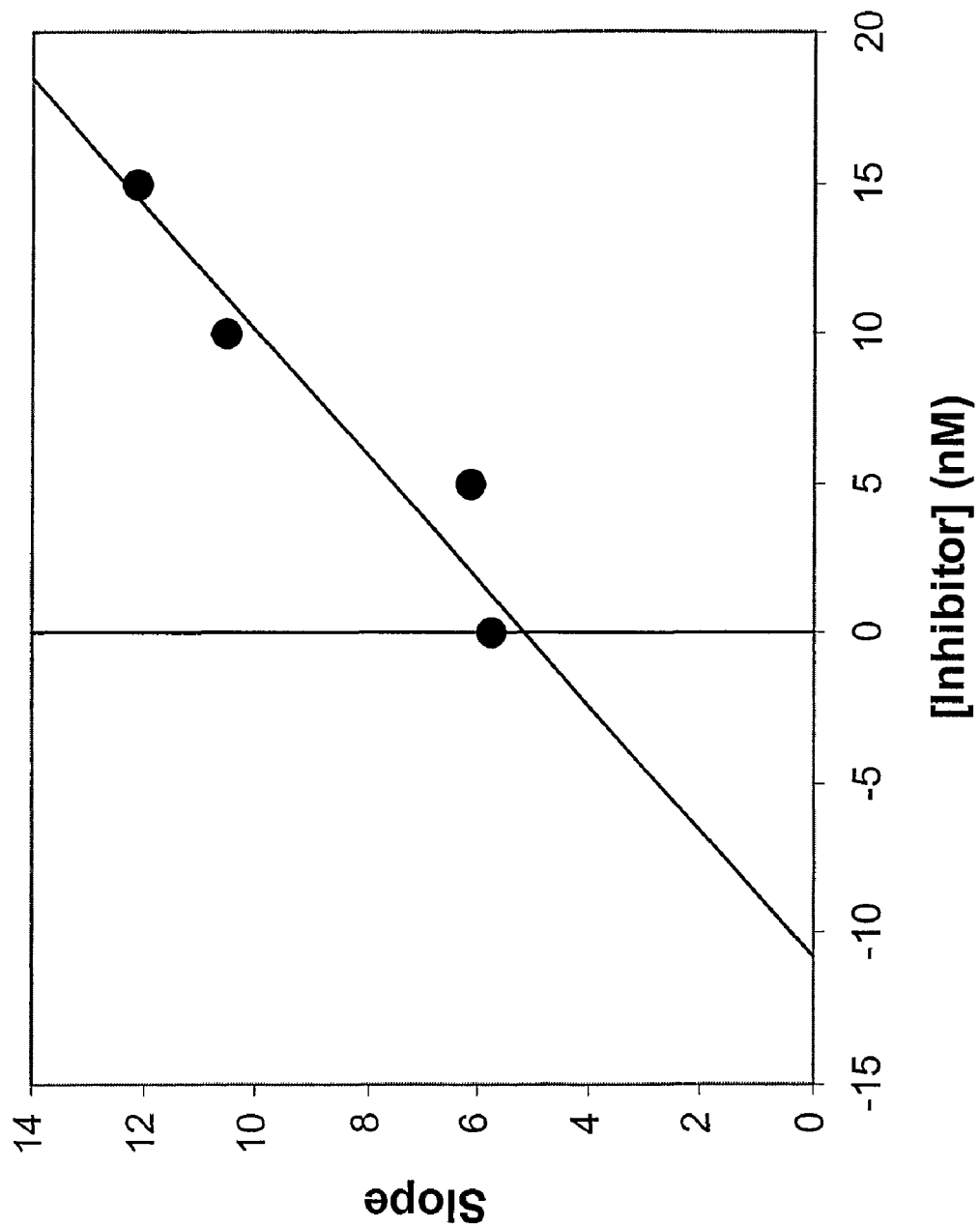

FIG. 6 shows the slope replot used to estimate the KI of the 29-mer. Slope values $(K_M/V_{max})(1+([I]/KI))$ for each inhibitor concentration from experimental data in FIG. 5 were determined using a non-linear regression computer program (Enzyme $Kinetics$, v. 1.2, Trinity software). Slope values were then plotted verses each of the corresponding inhibitor values. The x-axis intercept in this plot is $-K_I$.

Figure 7:
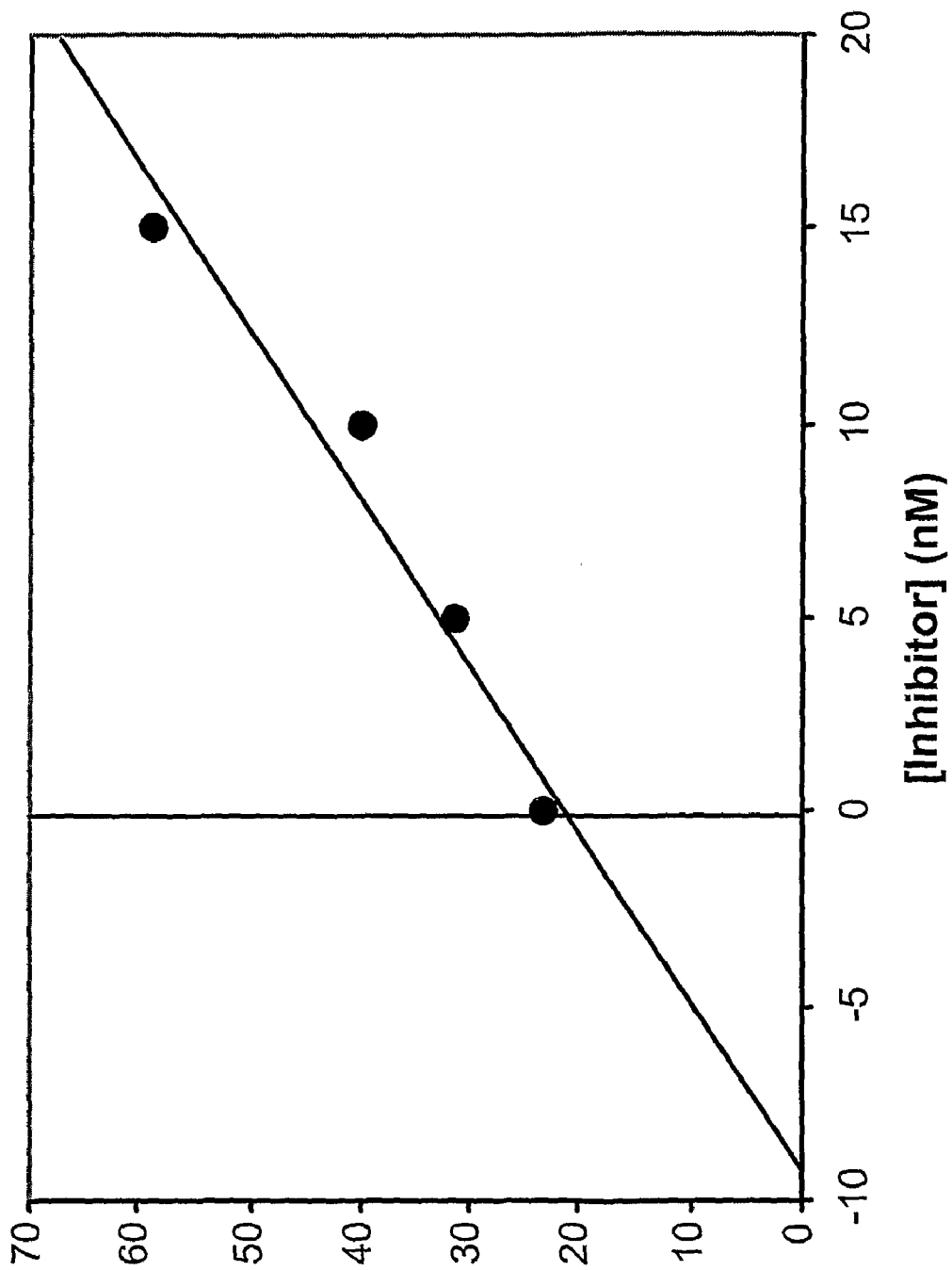

FIG. 7 shows the intercept replot to estimate the $K_I'$ of the 29-mer. Intercept values $(1/V_{max})(1+([I]/K_I'))$ for each inhibitor concentration from experimental data in FIG. 5 were determined using a non-linear regression computer program (Enzyme Kinetics, v. 1.2, Trinity software). Intercept values were then plotted verses each of the corresponding inhibitor values. The x-axis intercept in this plot is $-K_I'$.

Figure 8:
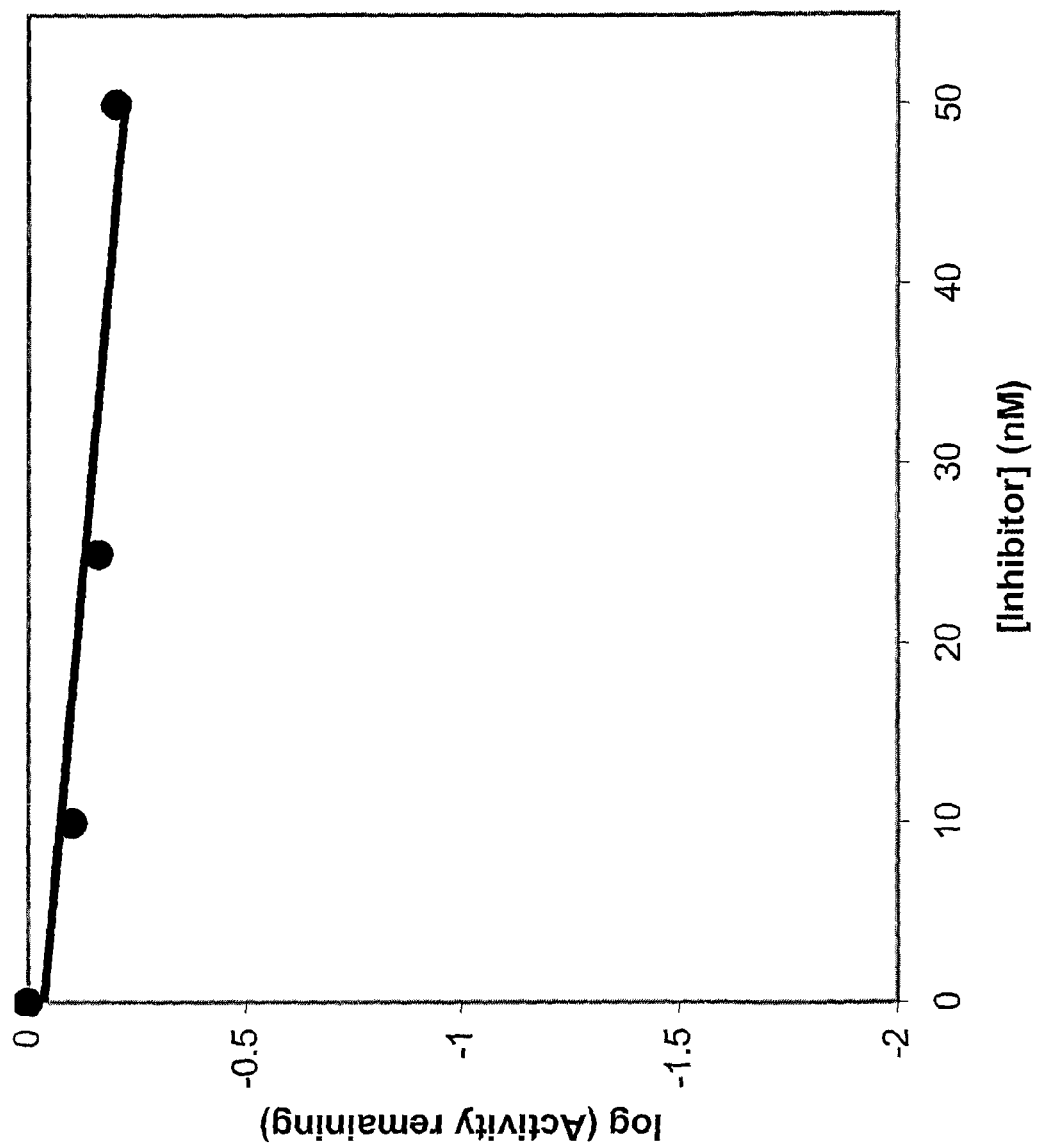

Since the enzyme requires the presence of zinc in the active site, the $IC_{50}$ value of the 29-mer was redetermined in the presence of excess zinc. This resulted in an $IC_{50}$ value of 92.1 nM, showing dependence on the zinc concentration, as shown in FIG. 8 and Table 1.

TABLE 1

Inhibition of *B. cereus* 5/B/6 metallo-β-lactamase by synthetic 29-mer.

| Oligomer | $IC_{50}$ | $K_I$ | $K_I'$ |
|---|---|---|---|
| 29-mer $[Zn^{2+}] = 0$ | 14 nM | 11 nM | 9.1 nM |
| 29-mer $[Zn^{2+}] = 1$ mM | 92 mM | — | — |

FIG. 8 shows the determination of the $IC_{50}$ for *B. cereus* metallo-β-lactamase by the 29-mer. The enzyme was incubated in the buffer (MOPS pH=7.0 and 1 mM $ZnSO_4$) for 15 minutes at 30° C. The concentration of the substrate (cephalosporin C) is 4 mM.

In order to check if the reversible inhibition was dependent on time, the enzyme was incubated with 10 nM of 29-mer and the inhibition was measured for time dependence. Experiments showed that after incubations of various times that there was essentially no time dependence of the inhibition, as shown in FIG. 9.

Figure 9:
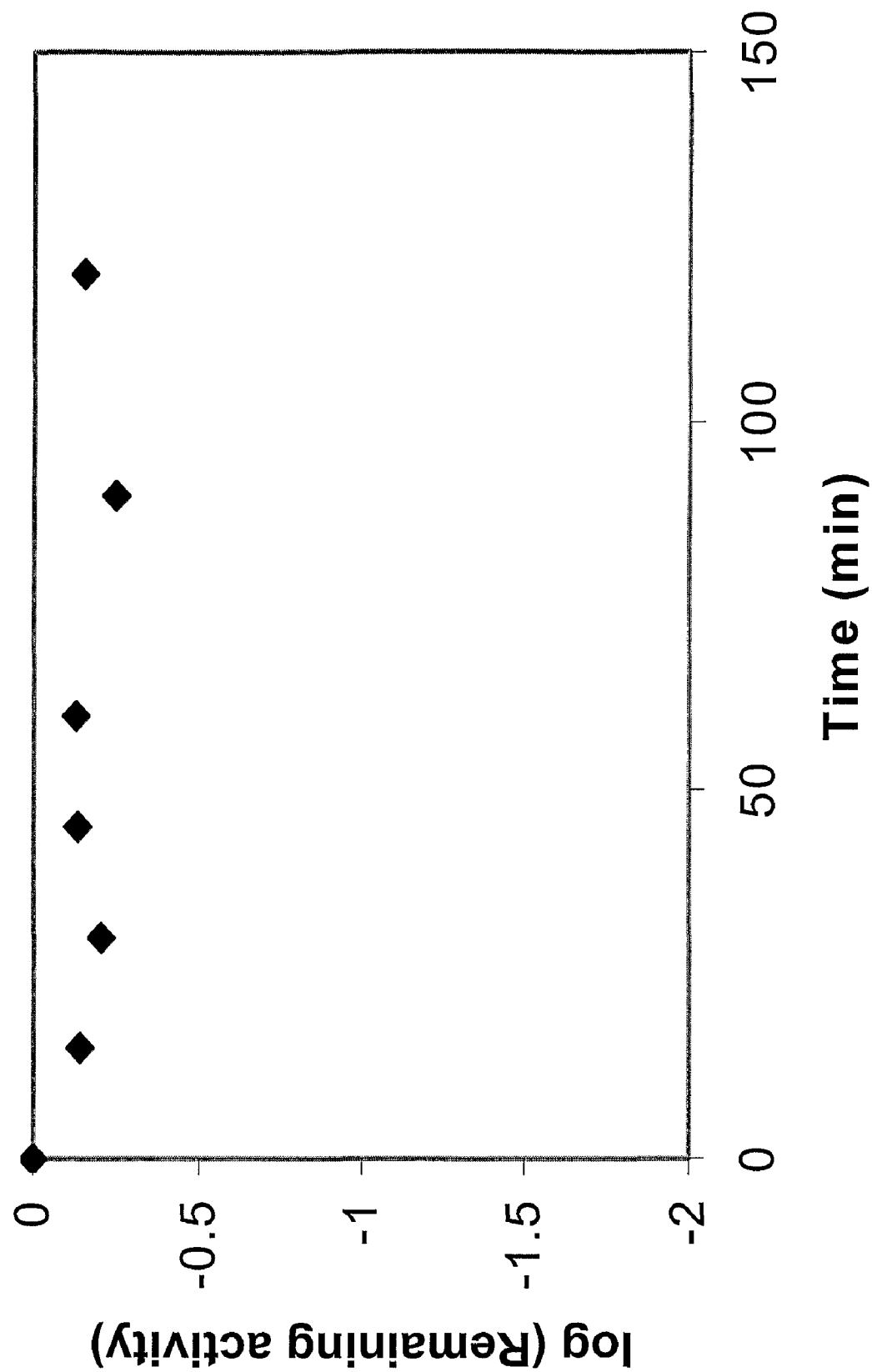

FIG. 9 shows the determination of the time dependence of the 29-mer with metallo-β-lactamase. The enzyme was incubated with 10 nM 29-mer in buffer (50 mM MOPS) at 30° C. for the specified times.

Specificity of the inhibitor for metallo-β-lactamase was demonstrated by testing the inhibitor against *B. cereus* 569/H/9 β-lactamase I (class A β-lactamase). Additionally a bovine carboxypeptidase A ($Zn^+$ dependent enzyme) assay was performed to test for $Zn^{2+}$ chelation specificity. Experiments with 29-mer concentrations of 375 nM (25 times the metallo-β-lactamase $IC_{50}$) resulted in no inhibition in both cases (data not shown).

Although not wanting to be bound by theory, the noncompetitive inhibition pattern is reminiscent of EDTA and 2-mercaptoethanol, both of which are metal ion chelators (Kim, 2002). Taking into account the dependence of the inhibitor on the concentration of $Zn^{2+}$ present, it suggests that the inhibitor is involved in complexation with the $Zn^{2+}$ ion in the active site. This result is similar to other inhibitors of metallo-β-lactamase that are known to complex with the zinc ion resulting in inactivation (Mollard et al, 2001, Garcia-Saez, 2003).

Example 2

Figure 10:
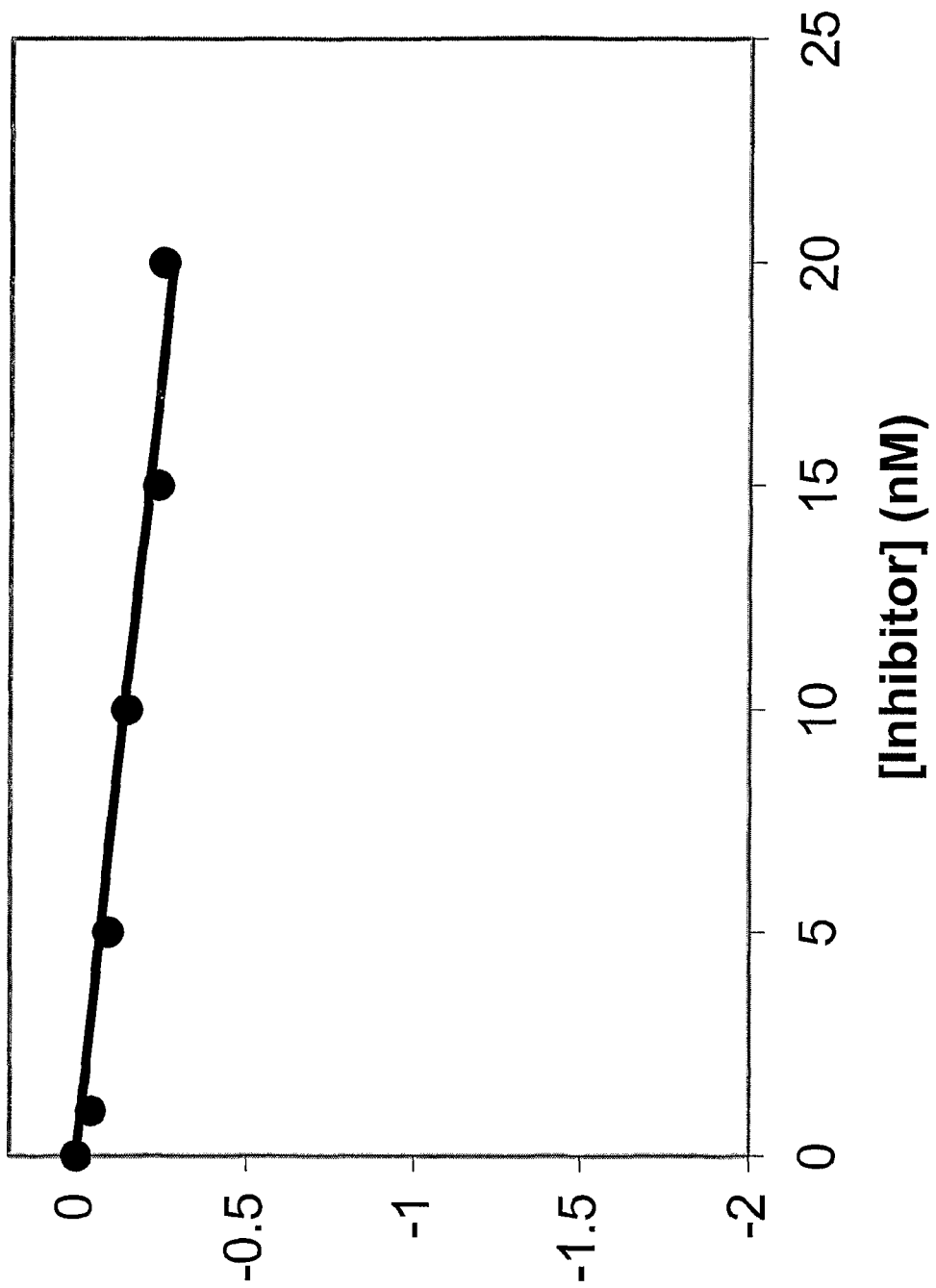

The 15-mer (SEQ ID No.5). In order to determine which part of the aptamer was binding to the enzyme two individual aptamers consisting of the first fifteen base pairs (SEQ ID No. 5) and the last fourteen base pairs (SEQ ID No.: 6) were synthesized so that each could be tested as an inhibitor. The 15-mer (SEQ ID No. 5) was made first and the $IC_{50}$ was determined to be 21 nM, as shown in FIG. 10. FIG. 10 shows the determination of the $IC_{50}$ for *B. cereus* metallo-β-lactamase by the 15-mer (SEQ ID No. 5). The enzyme was incubated in the buffer (MOPS pH=7.0) for 15 minutes at 30° C. The concentration of the substrate (cephalosporin C) is 4 mM.

Figure 11:
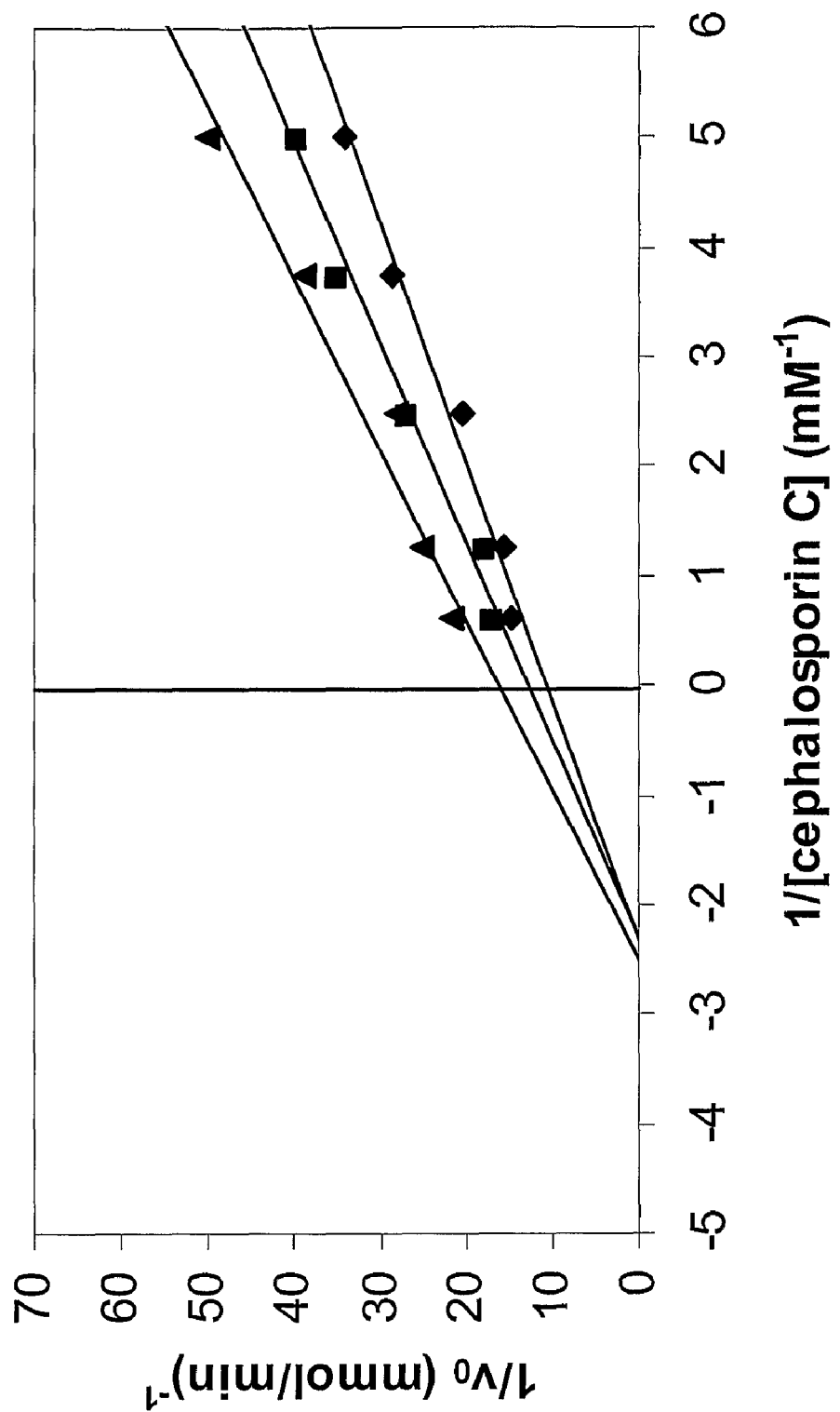

As with the 29-mer (SEQ ID No. 4), a steady state kinetic study of the 15-mer (SEQ ID No. 5) was performed, producing a noncompetitive inhibition pattern of the enzyme, as shown in FIG. 13. FIG. 11 shows a Lineweaver-Burk plot of the inhibition of *B. cereus* 5/B/6 metallo-β-lactamase the by 15-mer. Diamond: [I]=0 nM; Square: [I]=20 nM; Triangle: [I]=40 nM. Replots of the slope and intercept gave a $K_1$ value of 103 nM (FIG. 12) and a $K_I'$ value of 76.5 nM, as shown in FIG. 13. FIG. 13 shows the slope replot to estimate the $K_I'$ of the 15-mer ((SEQ ID No. 5). Slope values $(1/V_{max})(1+([I]/K_I'))$ for each inhibitor concentration from experimental data in FIG. 11 were determined using a non-linear regression computer program (Scientific Data Analysis Software, Version 1.1 Prentice Hall). Slope values were then plotted verses each of the corresponding inhibitor values. The x-axis intercept in this plot is $-K_I'$.

Figure 12:
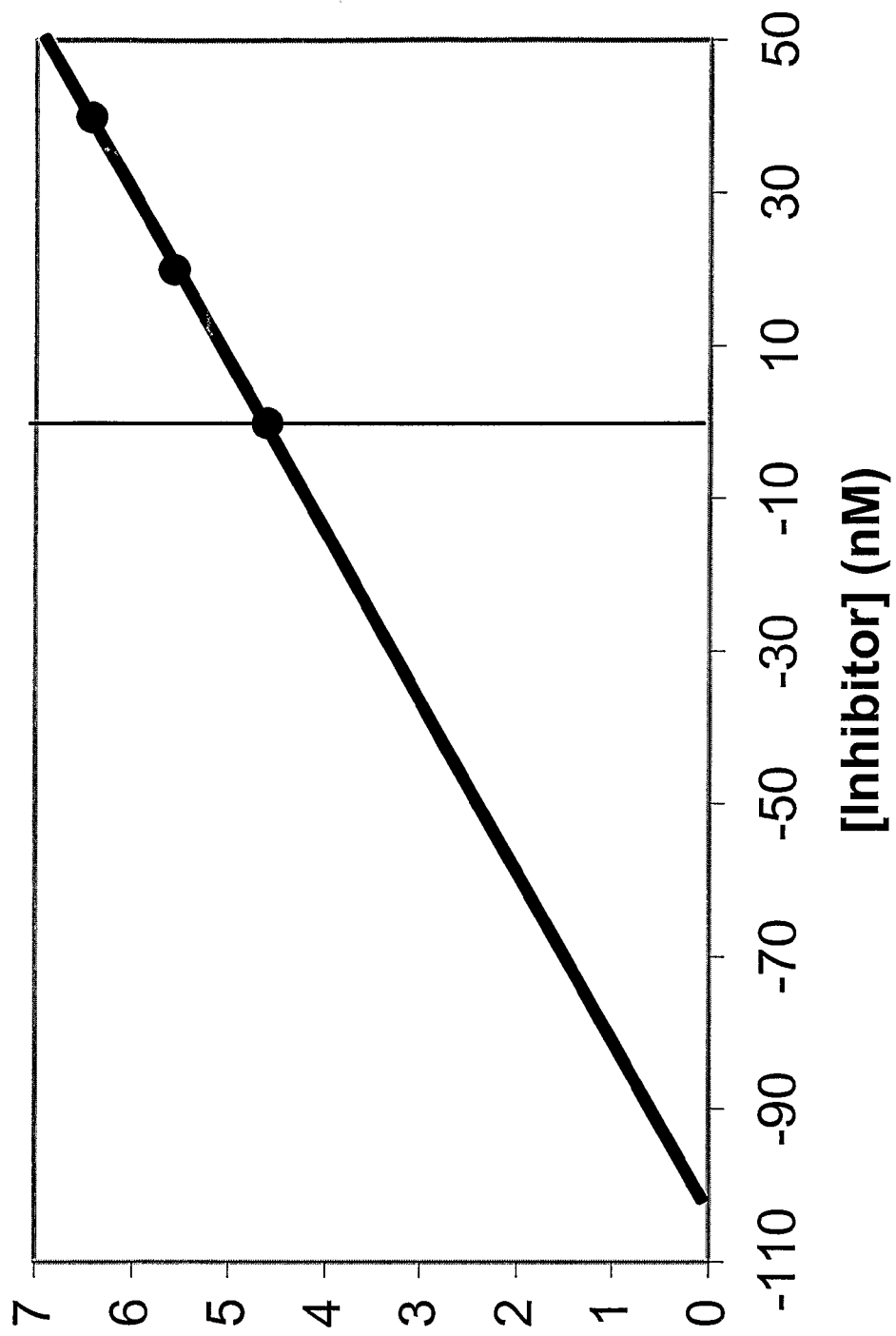

FIG. 12 shows the lope replot to estimate the $K_I$ of the 15-mer (SEQ ID No. 5). Slope values $(K_M/V_{max})(1+([I]/K_I))$ for each inhibitor concentration from experimental data in FIG. 11 were determined using a non-linear regression computer program (Scientific Data Analysis Software, Version 1.1, Prentice Hall). Slope values were then plotted verses each of the corresponding inhibitor values. The x-axis intercept in this plot is $-K_I$.

Testing of the subfragments of the 29-mer produced some results consistent with the results obtained by Kim (2002). The 15-mer produced an $IC_{50}$ of 21 nM, which is slightly higher than the 29-mer, as well as producing a noncompetitive inhibition pattern assay. Steady state kinetic data showed decreased affinity that is not surprising due to the increased $IC_{50}$. Since there was no improvement in the inhibition kinetics compared to the 29-mer no further experiments were preformed with the 15-mer.

The complementary single strands of the 15-mer were tested for inhibition of the metallo-β-lactamase. This was preformed to see if the presence of nonhybridized single-strand DNA molecules had an effect on the inhibition. Each strand had a dramatically higher $IC_{50}$ than either the double-stranded 29-mer or double-stranded 15-mer. Due to the high $IC_{50}$ produced we believe that the $IC_{50}$ for the both of the double-stranded inhibitors is not resultant from nonhybridized single-stranded DNA. This also suggests that the double-stranded structure of the oligonucleotides is important in the inhibition of the metallo-β-lactamase enzyme.

Example 4

The 14-mer (SEQ ID No.6). In order to determine which part of the aptamer was binding to the enzyme two individual aptamers consisting of the first fifteen base pairs (SEQ ID No. 5) and the last fourteen base pairs (SEQ ID No.: 6) were synthesized so that each could be tested as an inhibitor. The 14-mer (SEQ ID No.: 6) produced a slightly lower $IC_{50}$ of (11 nM) than the 29-mer suggesting this portion of the 29-mer is likely responsible for the inhibition. A noncompetitive inhibition pattern assay was again produced, however, the $K_I$ and $K_I'$ values were slightly higher than those of the 29-mer.

Due to the close similarities in the kinetic inhibition data for the double-stranded 29-mer and double-stranded 14-mer (SEQ ID No.: 6) further experiments were used to test its specificity. The specificity of the 14-mer (SEQ ID No.: 6) was tested using the class A β-lactamase from *B. cereus* 569/11/9 and bovine carboxypeptidase A enzymes used for the 29-mer specificity experiments. As expected there was no inhibition of the class A β-lactamase, which again shows that the inhibition caused, by the 14-mer, like the 29-mer, is not related solely, to the substrate-binding site. In contrast, the 14-mer inhibited the bovine carboxypeptidase A enzyme, which as mentioned above is $Zn^{2+}$ dependent, with an $IC_{50}$ value of 100 nM. Although not wanting to be bound by theory, this suggests that there is coordination of the $Zn^{2+}$ ion(s) in the active site of the metallo-β-lactamase as mentioned above. While the double-stranded 14-mer is nearly identical to the double-stranded 29-mer in terms of metallo-β-lactamase inhibition, excision of the double-stranded 15-mer (SEQ ID No.: 5) sequence from the 29-mer gave a less specific inhibition (14-mer, SEQ ID No.: 6).

Although these values were higher than the 29-mer (SEQ ID No.: 4), each of the complementary strands was tested to determine their $IC_{50}$ values. The ssDNA of 5'-(dATGATCCGGTGCTGT)-3' (SEQ ID No. 5) produced an $IC_{50}$ of 0.15 µM and the ssDNA of 5'-(dACAGCACCGGATCAT)-3'(SEQ ID No. 7) produced an $IC_{50}$ of 0.75 µM (data not shown). The ds14-mer was then made and the $IC_{50}$ for this aptamer produced a value of 11 nM (FIG. 13, and Table 2). FIG. 13 shows the determination of the $IC_{50}$ for B. cereus metallo-β-lactamase by the 14-mer. The enzyme was incubated in the buffer (MOPS pH=7.0) for 15 minutes at 30° C. The concentration of the substrate (cephalosporin C) is 4 mM.

TABLE 2

Inhibition of B. cereus 5/B/6 metallo-β-lactamase by synthetic ss- and dsDNA.

| Oligomer | $IC_{50}$ | $K_I$ | $K_I'$ |
|---|---|---|---|
| ds15-mer | 21 nM | 103 nM | 76.5 nM |
| ssDNA 5'(dATGATCCGGTGCTGT)3' | 0.15 µM | — | — |
| ssDNA 5'(dACAGCACCGGATCAT)3' | 0.75 µM | — | — |
| ds14-mer | 11 nM | 13 nM | 13 nM |

A steady-state kinetic study was preformed with the double-stranded 14-mer (SEQ ID No.: 6). Again, the same type of noncompetitive inhibition pattern as with the double-stranded 29-mer and double-stranded 15-mer (SEQ ID No.: 5) was observed (FIG. 14). FIG. 14 shows a Lineweaver-Burk plot of the inhibition of B. cereus 5/B/6 metallo-β-lactamase the by 14-mer (SEQ ID No.: 6) (Diamond: [I]=0 nM; Square: [I]=5 nM; Triangle: [I]=10 nM. I=14-mer).

Replots of the slope and intercept gave a $K_I$ value of 13 nM (FIG. 15) and a $K_I'$ value of 13 nM (FIG. 16, Table 2). FIG. 15 shows the slope replot to estimate the $K_1$ of the 14-mer. Slope values $(K_M/Vmax)(1+([I]/K_I))$ for each inhibitor concentration from experimental data in FIG. 14 were determined using a non-linear regression computer program (Enzyme Kinetics, v. 1.2, Trinity software). Slope values were then plotted verses each of the corresponding inhibitor values. The x-axis intercept in this plot is $-K_I$.

FIG. 16 shows the intercept replot to estimate the $K_I'$ of the 14-mer. Intercept values $(1/V_{max})(1+([I]/K_I'))$ for each inhibitor concentration from experimental data in FIG. 14 were determined using a non-linear regression computer program (Enzyme Kinetics, v. 1.2, Trinity software). Intercept values were then plotted verses each of the corresponding inhibitor values. The x-axis intercept in this plot is $-K_I'$.

In order to check if the reversible inhibition by the 14-mer (SEQ ID No.: 6) was dependent on time, the enzyme was incubated with 10 nM of 14-mer and the inhibition was measured for time dependence. Experiments showed that after incubations of various times that there was essentially no time dependence of the inhibition (FIG. 17). FIG. 17 shows determination of the time dependence of the 14-mer (SEQ ID No.: 6) with metallo-β-lactamase. The enzyme was incubated with 10 nM 14-mer in buffer (50 mM MOPS) at 30° C. for the specified times.

The specificity of the inhibitor for metallo-β-lactamase was demonstrated by testing the 14-mer (SEQ ID No.: 6) against *B. cereus* 569/H/9 β-lactamase I (class A β-lactamase). At 25 times the $IC_{50}$ value (275 nM) for the metallo-β-lactamase no inhibition of the against *B. cereus* 569/H/9 β-lactamase I was detected (data not shown) Additionally a bovine carboxypeptidase A ($Zn^{2+}$ dependent enzyme) assay was performed to test for $Zn^{2+}$ specificity. The 14-mer was found to inhibit the bovine carboxypeptidase A and an $IC_{50}$=100 nM was determined (FIG. 18). FIG. 18 shows the determination of the $IC_{50}$ for bovine carboxypeptidase A by the 14-mer. The enzyme was incubated in the buffer (10% LiC1) for 15 minutes at 30° C. The concentration of the substrate (Hippuryl-L-phenylalanine) is 1 mM.

One aspect of the current invention involves the understanding of the interactions that result in the ability of the three specific oligonucleotides ((SEQ ID Nos.: 4, 5, and 6) to act as inhibitors of the metallo-β-lactamase. Although not wanting to be bound by theory, this invention probably utilizes characteristics of known DNA-binding proteins. More specificity, the binding of double-stranded DNA-protein complexes has been shown to involve at least two different interactions. First, the sequence of the purine and pyrimidine nucleotides has been shown to provide unique patterns of hydrogen bond donors and acceptors (to and from proteins) in both the major and minor grooves. However, these are not the same hydrogen bonds that are involved in the base pair interactions, but those at the edge of the base pairs presented at the major groove, therefore the DNA maintains its double-stranded structure. The pattern of hydrogen donor and acceptors in the major grove is unique to each of the Watson-Crick base pairs and allows the protein to identify different sequences (Seeman, et al., 1976; Draper, 1995). The second interaction involves the phosphate and sugar moieties of the nucleic acid with the protein. This interaction is much less dependent on the sequence of the nucleic acid, but can provide stability to the formation of the complex (von Hipple and McGhee, 1972; Draper, 1995). Regardless of the mechanism for which they act, SEQ ID No.: 4, SEQ ID No.: 5, and SEQ ID No.: 6 act as inhibitors for metallo-β-lactamase.

The 29-mer, 15-mer and 14-mer double stranded DNA ligands describe herein are effective inhibitors of metallo-β-lactamase. Other known inhibitors of metallo-β-lactamases that have been identified have $IC_{50}$ values in the micromolar range (Garcia-Saez, I., et. al., 2003; Payne et al., 1997; Yang and Crowder, 1999; Scrofani et al., 1999); one exception is a tricyclic natural product with an $IC_{50}$ value of 300 nM (Payne et al., 2002). The compositions and methods described herein are by no means all-inclusive, and further methods to suit the specific application will be apparent to the ordinary skilled artisan. The scope of the double stranded ligands covered by this invention extends double stranded DNA ligands that bind lactamase and metallo-lactamases. Moreover, the effective amount of the compositions to inactivate lactamase in bacteria can be further approximated through analogy to compounds known to exert the desired effect.

Example 5

In order to test the in vivo efficacy of any of the oligonucleotide inhibitors discussed above, we can pipette a 40 μl solution of 0.16 mM cephalxin and various concentrations of the oligonucleotide to be tested onto a 1 cm diameter disk of sterile filter paper. The filter paper can be aseptically transferred to the surface of a agar plate of a Bacillus cereus 5/B/6 culture inoculated from an overnight liquid culture. The plates can be incubated at 30° C. for 10 hrs and examined for bacterial growth near the edges of the filter paper disk. Control disks can be prepared that contain only the antibiotic and not the oligonucleotide. Plates that have disks with the oligonucleotide that have no bacterial growth near the filter edges indicate that the oligonucleotide can inhibit metallo-β-lactamases in vivo.

REFERENCES CITED

The following U.S. Patents and references, to the extent that they provide exemplary procedural or other details supplementary to those set forth herein, are specifically incorporated herein by reference.

U.S. Patent Documents

U.S. Pat. No. 5,270,163 issued to Gold, et al., on Dec. 14, 1993, titled "Methods for Identifying Nucleic Acid Ligands."

U.S. Pat. No. 5,874,218 issued to Drolet et al., on Feb. 23, 1999, titled "Method for Detecting a Target Compound in a Substance using a Nucleic Acid Ligand"

U.S. Pat. No. 6,730,482 issued to Gold et al., on May 4, 2004, titled "Modified SELEX Processes without purified protein."

References

Abraham, E. P. and Waley, S. G. (1979) in *Beta-lactamases* (Hamilton-Miller, J. M. T. and Smith, J. T., eds.) pp. 311-338, Academic Press, New York.

Alberts, I. L., Katalin, N. and Wodak, S. J. (1998) "Analysis of Zinc Binding Sites in Protein Crystal Structures." *Protein Science* 7, 1700-1716.

Ambler, R. P. (1980) "The Structure of β-lactamases." *Phil. Trans. R. Soc. Lond. B*289, 321-331.

Ambler, R. P., Coulson, A. F. W., Frere, J.-M., Ghysen, J.-M., Joris, B., Forsman, M., Levesque, R. C., Triaby, G. and Waley, S. G. (1991) "A Standard Numbering Scheme for the Class A β-lactamases." *Biochem. J.* 276, 269-270.

Baker, D. W., and Rothberg, P. G. (1998) "An Unexpected Product From Polymerase Chain Reaction-Mediated Site-Directed Mutagenesis Due to Misalignment of the Mismatched Primer." *Molecular Diagnosis* 3, 157-161.

Bouagu, S., Laws, A., Galleni, M. and Page, M. (1998) "The Mechanism of Catalysis and the Inhibition of the *Bacillus Cereus* Zinc-Dependent β-lactamase." *Biochem. J.* 331, 703-711.

Brenner, D. G. and Knowles, J. D. (1984) Penicillanic Acid Sulfone: "Nature of Irreversible Inactivation of RTEM β-Lactamase from *Escherichia coli." Biochemistry* 23, 5834-5846.

Brown, T. A. (1998) in *Molecular Biology Labfax, 2nd ed.* 1, 147-148

Buynak, J. D., Chen, H., Vogeti, L., Gadhachanda, V. R., Bechanan, C. A., Shaw, R. W., and Palzkill, T. (2004) "Penicillin-Derived Inhibitors that Simultaneously Target both Metallo- and Serine-β-lactamases." *Bioorganic and Medicinal Chemistry Letters* 14, 1299-1304.

Carfi, A., Pares, S., Duee, E., Galleni, M., Duez, C., Frere, J. M. and Dideberg, O. (1995) "The 3-D structure of a Zinc Metallo-β-lactamase from *Bacillus Cereus* Reveals a New tType of Protein Fold." *The EMBO Journal,* 14, No. 20, 4914-4921.

Concha, N. O., Rasmussen, B. A., Bush, K. and Herzberg, O. (1996) "Crystal Structure of the Wide-Spectrum Binuclear Zinc β-lactamase from *Bacteroides Fragilis." Structure* 4, 823-836.

Danziger, L. H. and Pendland, S. L. (1995) "Bacterial resistance of β-lactam Antibiotics." *Am. J. health Syst. Pharm.* 52 (Suppl 2), S3-8.

Draper, D. E. (1995) "Protein-RNA Recognition." *Annu. Rev, Biochem.* 64, 593-620.

Ellington, A. D. and Szostak, J. W. (1990) "In Vitro Selection of RNA Molecules that Bind Specific Ligands." *Nature* 346, 818-822

Fisher, J., Charnas, R. L, Bradley, S. M. and Knowles, J. R. (1981) "Inactivation of the RTEM β-lactamase from *Escherichia Coli*. Interaction of Penam Sulfones With Enzyme." *Biochemistry* 20, 2726-2731.

Folk, J. E. and Schirmer, E. W. (1963) "The porcine pancreatic carboxypeptidase A." System. J. Biol. Chem. 238, 3884-3894.

Frere, J. M. (1995) "Beta-lactamases and Bacterial Resistance to Antibiotics." *Mol. Microbiol.* 16 (3), 385-395.

Garcia-Saez, I., Hopkins, J., Papamicael, C., Franceschini, N., Amicosante, G., Rossolini, G. M., Galleni, M., Frere, J., Dideberg, O. (2003) "The 1.5-A Structure of *Chryseobacterium Meningosepticum* Zinc β-lactamase in Complex with the Inhibitor, D-Captopril." *J. Biol. Chem.* 278 (26), 23868-23873.

Ghuysen, J.-M. (1988) in *Antibiotic Inhibition of Bactrial Cell Surface Assembly and Function* (Actor, P., Daneo-Moore, L., Higgins, M. L., Salton, M. R. J. and Shockman, G. D., Ed.) pp. 268-284, American Society for Micro biology, Washington, D.C.

Gold, L., Polisky, B., Uhlenbeck, O. and Yarus, M., (1995) "Diversity of Oligonucleotide."*Functions. Annu. Rev. Biochenz.* 64, 763-797

Hanahan, D. (1983) "Studies on Transformation of *Escherichia Coli* with Plasmids." J. Mol. Biol. 166, 557-580

Joris, B., Ledent, P., Dideberg, O., Fonze, E., Lamotte-Brasseur, J., Kelly, J. A., Ghuysen, J.-M. and Frere, J.-M. (1991) "Comparison of the Sequences of Class A β-lactamases and of the Secondary Structure elements of Penicillin-recognizing *Proteins." Antimicrob. Agents Chemother.* 35, 2294-2301.

Joyce, G. F. (1998) "Amplification, Mutation and Selection of Catalytic RNA." Gene 82, 83-87.

Kelly, J. A., Knox, J. R., Moews, P. C., Moring, J. and Zhao, H. C. (1988) in *Antibiotic Inhibition of Bactrial Cell Surface Assembly and Function* (Actor, P., Daneo-Moore, L., Higgins, M. L., Salton, M. R. J. and Shockman, G. D., Ed.) pp. 261-267, American Society for Micro biology, Washington, D.C.

Kim, S. K. (2002) "Inhibition of Metallo-Beta-Lactamase by Rational and Combinatorial Approaches." Ph.D. thesis, Texas Tech University Klug, S. J., and Famulok, M. (1994) "All You Wanted to Know About SELEX." *Molecular Biology Reports* 20, 97-107

Livermore, D. M. (1991) "Mechanisms of Resistance to β-lactam Antibiotics." *Scand. J. Infect. Dis., Suppl.* 78, 7-16

Lowery, O. H., Rosenberg, N. J., Farr, A. L., and Randall, R. J. (1951) "Protein Measurement With the Folin Phenol Reagent." *J. Biol. Chem.* 193, 265-275

Maugh, T. M. (1981) "New Wave of Antibiotics Builds." *Science* 214, 1225-1228.

Maxam, A. M. and Gilbert, W. (1977) "A New Method for Sequencing DNA." *Proc. Natl. Acad. Sci. USA* 74, 560-564.

Mollard, C., Moali, C., Papamicael, C., Damblon, C., Vessilier, S., Amicosante, G., Schofield, C. J., Galleni, M., Frere, J. M. and Roberts, G. C. (2001) "Thiomandelic Acid, a Broad Spectrum Inhibitor of Zinc β-Lactamases." *J. Biol. Chem.* 276, 45015-45023.

Payne, D. J., Bateson, J. H., Gasson, B. C., Proctor, D., Khushi, T, Farmer, T. H., Tolson, D. A., Bell, D., Skett, P. W., Marshall, A. C., Reid, R., Ghosez, L., Combret, Y. and Marchand-Brynaert, J. (1997) "Inhibition of Metallo-β-lactamases by a Aeries of Mercaptoacetic Acid Thiol Ester Derivatives." *Antimicrob. Agents Chemother.* 41, 135-140.

Pitout, J. D. D., Sanders, C. C. and Sanders, W. E. (1997) "Antimicrobial Resistance with Focus on β-lactam Resistance in Gram-negative Bacilli. *Am. J. Med.* 103, 51-59.

Rahil, J. and Pratt, R. F. (1991) "Phosphonate Nomoester Inhibitors of Class A β-Lactamases." *Biochem. J.* 275, 793-795.

Reddy, P., Peterkofsky, A. and McKenny, K. (1989) "Hyperexpression and Purification of *Escherichia coli* Adenylate Cyclase Using a Vector Designed Expression of Lethal Gene Products." *Nucleic Acids Res.* 17, 10473-10488.

Sambrook, J., Fritsch, E. F. and Maniatis, T. (1989) *Molecular Cloning: A Laboratory Manual,* 2ed, pp. 7.70-7.76, Cold Spring Harbor Laboratory Press, New York.

Scrofani, S. D., Chung, J., Huntley, J. J., Benkovic, S. J., Wright, P. E. and Dyson, H. J. (1999) "NMR Characterization of the Metallo-β-lactamase of *Bacteroids Fragilis* and its Interaction with a Tight-Binding Inhibitor: role of an active-site loop." *Biochemistry* 44, 14507-14514.

Seeman, N. C., Rosenberg, J. M., and Rich, A. (1976) "Sequence-specific recognition of double Helical Nucleic Acids by Proteins." *Proc. Nat. Acad. Sci.* 73, 804-808.

Shaw, R. W., Clark, S. D., Hilliard, N. P. and Harman, J. G. (1991) "Hyperexpression in *Escherichia coli*, Purification, and Characterization of the Metallo-β-lactamase of *Bacillus Cereus* 5/B/6." Prot. Exp. Purif. 2, 151-157.

Von Hippel P H, McGhee J D. (1972) "DNA-protein interactions." Annu Rev Biochem. 41(10):231-300.

Yang, K. W. and Crowder, M. W. (1999) "Inhibition Studies on the Metallo-β-lactamase L1 from *Stenotrophoinonas Maltophilia."* Arch. Biochem. Biophys. 368, 1-6.

---

What is claimed is:

1. An isolated double stranded DNA molecule consisting of SEQ ID NO: 4 that binds to a Class B metallo-β-lactamase in a solution with a salt concentration of between about 10 μM and about 50 μM NaCl.

2. The isolated double stranded DNA molecule of claim 1, wherein the Class B metallo-β-lactamase is SEQ ID NO: 8 or SEQ ID NO: 9.

3. The isolated double stranded DNA molecule of claim 2, wherein the Class B metallo-β-lactamase comprises a *B. cereus* 5/B/6 metallo-β-lactamase.

* * * * *

SEQUENCE LISTING

```
<160> NUMBER OF SEQ ID NOS: 9

<210> SEQ ID NO 1
<211> LENGTH: 61
<212> TYPE: DNA
<213> ORGANISM: Artificial Sequence
<220> FEATURE:
<223> OTHER INFORMATION: 61-mer Synthetic oligonucleotide.
<220> FEATURE:
<221> NAME/KEY: misc_structure
<222> LOCATION: (16)..(45)
<223> OTHER INFORMATION: "n" can be A, T, G or C.
<220> FEATURE:
<221> NAME/KEY: misc_feature
<222> LOCATION: (16)..(45)
<223> OTHER INFORMATION: n is a, c, g, or t

<400> SEQUENCE: 1
cgcgagctcc gcgcgnnnnn nnnnnnnnnn nnnnnnnnnn nnnnncgcgc gcatatggcg        60
c                                                                       61

<210> SEQ ID NO 2
<211> LENGTH: 16
<212> TYPE: DNA
<213> ORGANISM: Artificial Sequence
<220> FEATURE:
<223> OTHER INFORMATION: 16-mer Primer.

<400> SEQUENCE: 2
gcgccatatg cgcgcg                                                       16

<210> SEQ ID NO 3
<211> LENGTH: 15
<212> TYPE: DNA
<213> ORGANISM: Artificial Sequence
<220> FEATURE:
<223> OTHER INFORMATION: 15-mer Primer.

<400> SEQUENCE: 3
cgcgagctcc gcgcg                                                        15

<210> SEQ ID NO 4
```

```
<211> LENGTH: 29
<212> TYPE: DNA
<213> ORGANISM: Artificial Sequence
<220> FEATURE:
<223> OTHER INFORMATION: 29-mer Synthetic oligonucleotide.

<400> SEQUENCE: 4
atgatccggt gctgtatgtt cctacatga                                29

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide.

<400> SEQUENCE: 5
atgatccggt gctgt                                               15

<210> SEQ ID NO 6
<211> LENGTH: 14
<212> TYPE: DNA
<213> ORGANISM: Artificial Sequence
<220> FEATURE:
<223> OTHER INFORMATION: Synthetic oligonucleotide.

<400> SEQUENCE: 6
atgttcctac atga                                                14

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide.

<400> SEQUENCE: 7
acagcaccgg atcat                                               15

<210> SEQ ID NO 8
<211> LENGTH: 228
<212> TYPE: PRT
<213> ORGANISM: Artificial Sequence
<220> FEATURE:
<223> OTHER INFORMATION: Modified protein sequence.

<400> SEQUENCE: 8

Met Glu Arg Thr Val Glu His Lys Val Ile Lys Asn Glu Thr Gly Thr
1               5                   10                  15

Ile Ser Ile Ser Gln Leu Asn Lys Asn Val Trp Val His Thr Glu Leu
            20                  25                  30

Gly Tyr Phe Ser Gly Glu Ala Val Pro Ser Asn Gly Leu Val Leu Asn
        35                  40                  45

Thr Ser Lys Gly Leu Val Leu Val Asp Ser Ser Trp Asp Asp Lys Leu
    50                  55                  60

Thr Lys Glu Leu Ile Glu Met Val Glu Lys Lys Phe Lys Lys Arg Val
65                  70                  75                  80

Thr Asp Val Ile Ile Thr His Ala His Ala Asp Arg Ile Gly Gly Met
                85                  90                  95
```

```
Lys Thr Leu Lys Glu Arg Gly Ile Lys Ala His Ser Thr Ala Leu Thr
            100                 105                 110

Ala Glu Leu Ala Lys Lys Asn Gly Tyr Glu Glu Pro Leu Gly Asp Leu
        115                 120                 125

Gln Ser Val Thr Asn Leu Lys Phe Gly Asn Met Lys Val Glu Thr Phe
    130                 135                 140

Tyr Pro Gly Lys Gly His Thr Glu Asp Asn Ile Val Val Trp Leu Pro
145                 150                 155                 160

Gln Tyr Gln Ile Leu Ala Gly Gly Cys Leu Val Lys Ser Ala Ser Ser
                165                 170                 175

Lys Asp Leu Gly Asn Val Ala Asp Ala Tyr Val Asn Glu Trp Ser Thr
            180                 185                 190

Ser Ile Glu Asn Val Leu Lys Arg Tyr Gly Asn Ile Asn Leu Val Val
        195                 200                 205

Pro Gly His Gly Glu Val Gly Asp Arg Gly Leu Leu Leu His Thr Leu
    210                 215                 220

Asp Leu Leu Lys
225

<210> SEQ ID NO 9
<211> LENGTH: 215
<212> TYPE: PRT
<213> ORGANISM: Artificial Sequence
<220> FEATURE:
<223> OTHER INFORMATION: Modified protein sequence.
<220> FEATURE:
<221> NAME/KEY: MISC_FEATURE
<222> LOCATION: (26)..(26)
<223> OTHER INFORMATION: "Xaa" is any amino acid.
<220> FEATURE:
<221> NAME/KEY: MISC_FEATURE
<222> LOCATION: (172)..(172)
<223> OTHER INFORMATION: "Xaa" is any amino acid.

<400> SEQUENCE: 9

Val Ile Lys Asn Glu Thr Gly Thr Ile Ser Ile Ser Gln Leu Asn Lys
1               5                   10                  15

Asn Val Trp Val His Thr Glu Leu Gly Xaa Phe Asn Gly Glu Ala Val
            20                  25                  30

Pro Ser Asn Gly Leu Leu Leu Ser Thr Ser Lys Gly Leu Val Leu Val
        35                  40                  45

Asp Ser Ser Trp Asp Lys Leu Thr Lys Glu Leu Ile Glu Met Leu Glu
50                  55                  60

Lys Lys Phe Pro Lys Val Thr Asp Val Ile Ile Thr His Ala His Ala
65                  70                  75                  80

Asp Arg Ile Gly Gly Ile Lys Thr Leu Lys Glu Arg Gly Ile Lys Ala
                85                  90                  95

His Ser Thr Ser Leu Thr Ala Glu Leu Ala Lys Lys Ser Gly Tyr Glu
            100                 105                 110

Glu Pro Leu Gly Asp Leu Gln Ser Leu Thr Ser Leu Lys Phe Gly Asn
        115                 120                 125

Met Lys Val Glu Thr Phe Tyr Pro Gly Lys Gly His Thr Glu Asp Asn
    130                 135                 140

Ile Val Val Trp Leu Pro Gln Tyr Pro Leu Leu Val Gly Gly Cys Leu
145                 150                 155                 160
```

-continued

```
Val Lys Ser Ala Ala Lys Asp Leu Gly Asn Leu Xaa Asp Ala Tyr Val
            165                 170                 175

Asn Glu Trp Ser Thr Ser Ile Glu Asn Val Leu Lys Arg Tyr Ser Asn
            180                 185                 190

Ile Asn Ala Val Val Pro Gly His Gly Val Gly Asp Gly Leu Leu Leu
        195                 200                 205

His Thr Leu Asp Leu Leu Lys
    210                 215
```